United States Patent
Shewale et al.

(10) Patent No.: US 11,433,010 B2
(45) Date of Patent: *Sep. 6, 2022

(54) N-ACYL SARCOSINATE COMPOUNDS AND OXIDATIVE COMPOUNDS WITH IMPROVED STABILITY AND EFFICACY FOR USE IN PHARMACEUTICAL COMPOSITIONS

(71) Applicant: Micropure, Inc., Scottsdale, AZ (US)

(72) Inventors: Jaiprakash G. Shewale, Cave Creek, AZ (US); William E. Cooley, Wyoming, OH (US); James L. Ratcliff, Scottsdale, AZ (US); Esmeralda Ann Garcia-Smith, Centerton, AR (US)

(73) Assignee: Micropure, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/094,489

(22) Filed: Nov. 10, 2020

(65) Prior Publication Data

US 2021/0069073 A1    Mar. 11, 2021

Related U.S. Application Data

(63) Continuation-in-part of application No. 16/133,359, filed on Sep. 17, 2018, which is a continuation of application No. PCT/US2018/049302, filed on Sep. 3, 2018.

(60) Provisional application No. 63/089,469, filed on Oct. 8, 2020, provisional application No. 62/934,792, filed on Nov. 13, 2019, provisional application No. 62/676,170, filed on May 24, 2018, provisional application No. 62/553,450, filed on Sep. 1, 2017.

(51) Int. Cl.

| | |
|---|---|
| *A61K 8/20* | (2006.01) |
| *A61K 8/44* | (2006.01) |
| *A61Q 11/00* | (2006.01) |
| *A61K 8/21* | (2006.01) |
| *A61K 8/24* | (2006.01) |
| *A61K 8/29* | (2006.01) |
| *A61K 8/25* | (2006.01) |
| *A61K 8/9789* | (2017.01) |
| *A61K 8/34* | (2006.01) |
| *A61K 8/60* | (2006.01) |
| *A61K 8/06* | (2006.01) |
| *A61K 8/19* | (2006.01) |

(52) U.S. Cl.
CPC ............... *A61K 8/20* (2013.01); *A61K 8/06* (2013.01); *A61K 8/19* (2013.01); *A61K 8/21* (2013.01); *A61K 8/24* (2013.01); *A61K 8/25* (2013.01); *A61K 8/29* (2013.01); *A61K 8/34* (2013.01); *A61K 8/442* (2013.01); *A61K 8/60* (2013.01); *A61K 8/9789* (2017.08); *A61Q 11/00* (2013.01); *A61K 2800/43* (2013.01); *A61K 2800/48* (2013.01); *A61K 2800/52* (2013.01); *A61K 2800/92* (2013.01)

(58) Field of Classification Search
CPC ...... A61Q 11/00; A61Q 19/00; A61Q 17/005; A23V 2200/312; A61P 1/02; A61P 15/02; A61P 17/02; A61P 19/00; A61P 31/02; A61P 31/04; A61P 43/00; A61K 8/20; A61K 2800/92; A61K 8/0216; A61K 8/042; A61K 8/22; A61K 8/24
See application file for complete search history.

(56) References Cited

U.S. PATENT DOCUMENTS

| | | | |
|---|---|---|---|
| 8,980,229 B2* | 3/2015 | Pilch ........................ | A61K 8/19 424/49 |
| 2001/0006624 A1* | 7/2001 | Witt ........................ | A61K 8/20 424/53 |

* cited by examiner

*Primary Examiner* — Lezah Roberts
(74) *Attorney, Agent, or Firm* — Snell & Wilmer LLP

(57) ABSTRACT

Described herein are single-phase compositions and methods for its pharmaceutical and cosmetic use, comprising (i) a combination of N-acyl sarcosinate, (ii) an oxidative compound, and (iii) a buffering system in amounts and embodiments effective to protect the oxidative compounds from degradation prior to use and upon use and to enhance the efficacy of the composition in removing polymicrobial biofilms, reducing the re-growth of polymicrobial biofilms that leads to plaque formation, greater availability of chlorite ion for antimicrobial and cosmetic purposes, and effective oxidation of salivary biomolecules. When these single-phase compositions are comprised of a source of fluoride ion, they also achieve enhanced enamel fluoride uptake, higher enamel protection by enhanced remineralization and reduced demineralization of teeth when compared to US Pharmacopoeia Reference Dentifrice, prior known toothpastes comprising stabilized chlorine dioxide and comparable commercial dentifrices.

20 Claims, 5 Drawing Sheets

Confocal microscopy images of Toothpaste K and
water brushed specimens after 6 h of brushing

N-ACYL SARCOSINATE COMPOUNDS AND OXIDATIVE COMPOUNDS WITH IMPROVED STABILITY AND EFFICACY FOR USE IN PHARMACEUTICAL COMPOSITIONS

CROSS-REFERENCE TO RELATED APPLICATIONS

This application is a nonprovisional of and claims priority to U.S. Provisional Patent Application Ser. No. 63/089,469, filed on Oct. 8, 2020, entitled "ALIPHATIC ANIONIC COMPOUNDS WITH IMPROVED STABILITY AND EFFICACY FOR USE IN PHARMACEUTICAL COMPOSITIONS." This application is a nonprovisional of and claims priority to U.S. Provisional Patent Application Ser. No. 62/934,792, filed on Nov. 13, 2019, entitled "ALIPHATIC ANIONIC COMPOUNDS WITH IMPROVED STABILITY AND EFFICACY FOR USE IN PHARMACEUTICAL COMPOSITIONS." This application also claims priority to, the benefit of, and is a continuation in part of U.S. patent application Ser. No. 16/133,359, filed on Sep. 17, 2018, entitled "ALIPHATIC ANIONIC COMPOUNDS WITH IMPROVED STABILITY AND EFFICACY FOR USE IN PHARMACEUTICAL COMPOSITIONS." The '359 Application claims priority to and is a continuation of PCT Application No. PCT/US2018/049302, filed on Sep. 3, 2018, entitled "ALIPHATIC ANIONIC COMPOUNDS WITH IMPROVED STABILITY AND EFFICACY FOR USE IN PHARMACEUTICAL COMPOSITIONS." The '302 application claims priority to U.S. Provisional Patent Application No. 62/676,170 filed on May 24, 2018 entitled "ALIPHATIC ANIONIC COMPOUNDS AND OXIDATIVE COMPOUNDS WITH IMPROVED STABILITY AND EFFICACY FOR USE IN PHARMACEUTICAL COMPOSITIONS." The '302 application also claims priority to U.S. Provisional Patent Application No. 62/553,450 filed on Sep. 1, 2017 entitled "ALIPHATIC ANIONIC COMPOUNDS AND OXIDATIVE COMPOUNDS WITH IMPROVED STABILITY AND EFFICACY FOR USE IN PHARMACEUTICAL COMPOSITIONS." The contents of each of the foregoing applications are hereby incorporated by reference for all purposes (except for any subject matter disclaimers or disavowals, and except to the extent that the incorporated material is inconsistent with the express disclosure herein, in which case the language in this disclosure controls).

TECHNICAL FIELD

The present disclosure relates generally to a single-phase composition comprising a combination of compounds: a N-acyl sarcosinate compound, an oxidative compound, and a buffering system.

BACKGROUND

Oxidative compounds interact with various cellular components, causing, for example, peroxidation and disruption of membrane layers, oxidation of oxygen scavengers and thiol groups, enzyme inhibition, oxidation of nucleosides, impaired energy production, and/or disruption of protein synthesis and, possibly, cell death. Biomolecules produced by cells and various other chemical compounds also may be oxidized by the oxidative compounds.

Different compounds tend to interact with cellular components differently, producing differing biological results. For example, hydrogen peroxide may be more effective in controlling *Pseudomonas aeruginosa* and *Stenotrophomonas maltophilia* than peracetic acid (PAA). Similarly, PAA may be more effective than chlorine dioxide (C1O2) at preventing growth of *Escherichia coli, Listeria monocytogenes*, and *Salmonella typhimurium*. The biocidal activity of one oxidative compound or composition cannot readily predict the biocidal activity of another oxidative compound or composition. Sodium chlorite is a common source of chlorine dioxide.

Nonetheless, it may be desirable to add certain oxidative compounds to certain drug products and other therapeutic preparations, including prescription and over-the-counter products and preparations, including cosmetic preparations. Formulating and manufacturing such a product or preparation can be difficult however because of the reactivity of such oxidizing compounds, particularly at the required pH range and selecting other ingredients for such products or preparations. Among others, oxidative compounds may react chemically, such as with the hydroxy groups of alcohols and polyhydroxy compounds. For example, chlorine dioxide in aqueous solution with the desired pH range from about 6.0 to about 8.0 decomposes to the chlorite and chlorate ions. This chemical reaction pathway may lead to degradation of the oxidative compounds, the active ingredient(s), or other excipients in a single-phase composition. Such degradation may reduce the efficacy or needed shelf-life of the intended product. Accordingly, various challenges confront the manufacture of pharmaceutical and cosmetic products containing oxidative compounds. Thus, the achievement and maintenance of the stability of oxidizing compounds is an important and desired characteristic for commercial uses and applications.

One such product may be a fluoride toothpaste composition. Here, it may be desirable to maintain and extend the stability of the active ingredient(s) (e.g., fluoride ion), and other excipients, such as flavor, including stabilized source of chlorine dioxide or stabilized sodium chlorite. Stability may be considered to comprise from the time of manufacture, through distribution and sale, to the time of intended use.

The U.S. Pharmacopoeia (USP) defines the stability of a pharmaceutical product as "extent to which a product retains within specified limits and throughout its period of storage and use, i.e., its shelf life, the same properties and characteristics that it possessed at the time of its manufacture."; http://www.pharmacopeia.cn/v29240/usp29nf24s0_c1191.html (last visited September 2018).

SUMMARY

In accordance with various aspects, a single-phase composition is provided, as well as various formulations of the single-phase composition, including method of preparation, methods of administration and methods of use. In various embodiments, the single-phase composition may comprise N-acyl sarcosinate and a stabilized source of chlorine dioxide.

In various embodiments, a single-phase composition is provided, comprising: from about 0.01% to about 5.0% of N-acyl sarcosinate, based on a total weight of the single-phase composition; from about 0.001 to about 8% of an oxidative compound, based on a total weight of the single-phase composition; a buffering system, wherein pH of the single-phase composition is between 6.0 and 8.0; and water. In further embodiments, N-acyl sarcosinate facilitates stability of the oxidative compound. In further embodiments, N-acyl sarcosinate facilitates efficacy of the composition.

In further embodiments, the N-acyl sarcosinate is, at least one of, sodium lauroyl sarcosinate, sodium cocoyl sarcosinate, sodium myristoyl sarcosinate, sodium oleoyl sarcosinate, or sodium stearoyl sarcosinate.

In further embodiments, the oxidative compound is comprised of, at least one of, ammonium peroxydisulfate, carbamide (urea) peroxide, ferric chloride, hydrogen peroxide, potassium bromate, potassium chlorate, potassium perchlorate, potassium dichromate, potassium ferricyanide, potassium peroxymonosulfate, potassium persulfate, sodium bromate, sodium chlorate, sodium perchlorate, sodium chlorite, sodium hypochlorite, sodium iodate, sodium perborate, sodium percarbonate, sodium persulfate, stabilized chlorine dioxide, strontium peroxide, and zinc peroxide.

In certain aspects, the single-phase composition is formulated in at least one of an oral or nasal rinse, a gum, a gel, a paste, a cream, an oral or nasal spray, and a lozenge.

In various embodiments, the single-phase composition comprises an orally acceptable aqueous vehicle comprising, at least one, a humectant, an abrasive, a pharmaceutically acceptable carrier, a fluoride ion source, and a thickening agent.

In further embodiments, the single-phase composition oxidizes salivary biomolecules.

In further embodiments, the single-phase composition oxidizes salivary biomolecules in 30 to 120 seconds of contact with saliva.

In some embodiments, the salivary biomolecules are pyruvate and L-methionine.

In further embodiments, the single-phase composition is applied to, at least one of, anal, aural, nasal, oral, and urogenital cavities.

In further embodiments, less than 20% of the oxidative compound is destabilized after 3 months at 40±1° C. and 70-75% relative humidity or one year under ambient conditions.

In further embodiments, the oxidative compound is stabilized source of chlorine dioxide, wherein less than 20% of the stabilized chlorine dioxide is degraded after 3 months at 40±1° C. and 70-75% relative humidity or one year under ambient conditions.

In certain aspects, an oral care composition is provided, comprising: from about 0.01% to about 5.0% of an N-acyl sarcosinate, based on a total weight of the oral care composition; from about 0.001 to about 8% of an oxidative compound, based on the total weight of the oral care composition; a buffering system, wherein pH of the single-phase composition is between 6.0 and 8.0; and water, wherein the N-acyl sarcosinate provides enhanced stability and efficacy for the oxidative compound in the oral care composition.

In further embodiments, the oral care composition further comprises, at least one of, a humectant, a whitening agent, a thickening agent, a fluoride ion source, a sweetening agent, an abrasive, a flavoring agent, a coloring agent, and a gelling agent.

In further embodiments, the oral care composition is a dentifrice.

In further embodiments, less than 20% of the oxidative compound is degraded in 3 months at 40±1° C. and 70-75% relative humidity or one year under ambient conditions.

In various embodiments, the buffering system comprises disodium hydrogen phosphate and sodium dihydrogen phosphate.

In further embodiments, the oral care composition decreases regrowth of an oral polymicrobial biofilm.

In further embodiments, the oral care composition effectively reduces regrowth of the oral polymicrobial biofilm in 24 hours.

In further embodiments, the oral care composition enhances remineralization of tooth enamel more than US Pharmacopoeia (USP) Reference Dentifrice.

In further embodiments, the oral care composition oxidizes salivary biomolecules such as pyruvate and L-methionine in 30 to 60 seconds of contact with the saliva in the oral cavity.

In further embodiments, the oral care composition provides an increased amount of available chlorite ion.

In some aspects, a method for enhancing fluoride uptake into an oral cavity is provided, comprising: preparing an oral care composition comprising from about 0.01% to about 5.0% of an N-acyl sarcosinate, based on a total weight of the oral care composition, from about 0.001 to about 8% of an oxidative compound, based on the total weight of the oral care composition, a buffering system, wherein pH of the single-phase composition is between 6.0 and 8.0, water; and applying the oral care composition to the oral cavity.

In further embodiments, the enhanced fluoride uptake into the oral cavity is increased by about 1.2-fold.

In further embodiments, the enhanced fluoride uptake into the oral cavity is increased by about 1.7-fold.

In further embodiments, the oral care composition enhances fluoride uptake more than US Pharmacopoeia (USP) Reference Dentifrice.

In certain aspects, a method to decrease regrowth of oral polymicrobial biofilm is provided, comprising: preparing an oral care composition comprising from about 0.01% to about 5.0% of an N-acyl sarcosinate, based on a total weight of the oral care composition, from about 0.001 to about 8% of an oxidative compound, based on the total weight of the oral care composition, a buffering system, wherein pH of the single-phase composition is between 6.0 and 8.0, water; and applying the oral care composition to an oral cavity.

In further embodiments, the oral care composition decreases regrowth of oral polymicrobial biofilm.

The contents of this section are intended as a simplified introduction to the disclosure, and are not intended to limit the scope of any claim.

BRIEF DESCRIPTION OF THE DRAWING FIGURES

DETAILED DESCRIPTION

Definitions

Figure 1:
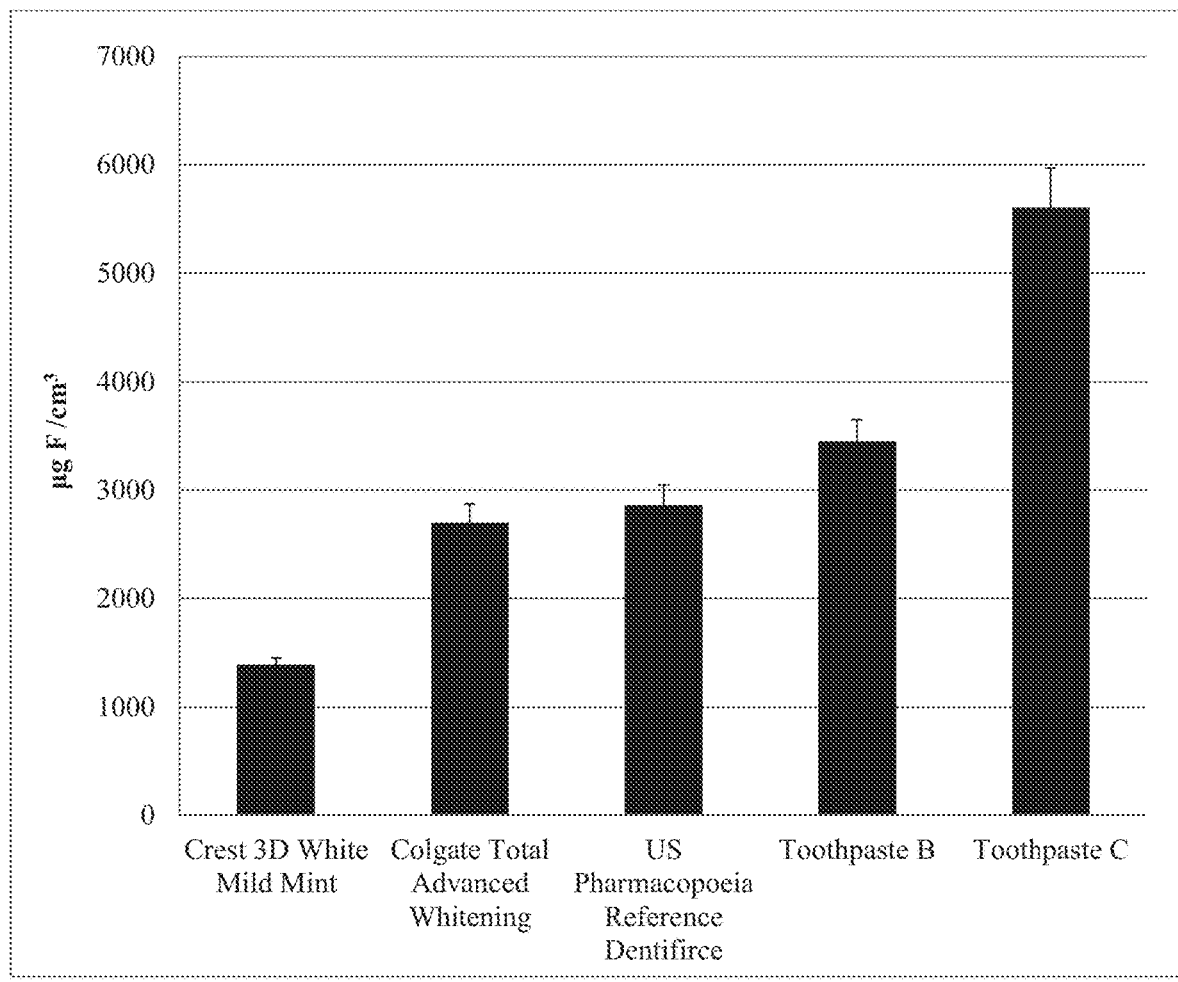
FIG. 1 is a graph illustrating fluoride uptake of commercial products and an oral care composition according to an embodiment.

The following is a list of definitions for terms used herein. Unless defined otherwise, all technical and scientific terms used herein generally have the same meaning as commonly understood by one of ordinary skill in the art. In the event that there is a plurality of definitions for a term herein, those in this section prevail unless stated otherwise. Generally, the nomenclature used herein and the laboratory procedures in cytopathicity analysis, microbial analysis, organic, physical and inorganic chemistry, and dental clinical research are those well-known and commonly employed in the art.

As used herein, "about" will be understood by persons of ordinary skill in the art and will vary to some extent on the context in which it can be used. Generally, "about" encompasses a range of values that are plus/minus 10% of a reference value, unless specifically defined. For instance, "about 25%" encompasses values from 22.5% to 27.5%.

As used herein, "acid source" means a biological material, usually a particulate material, or which is itself acidic or produces an acidic environment when in contact with liquid water or oxychlorine anion.

As used herein, "ambient conditions" means approximately room temperature (e.g., 20-35° C.) and relative humidity of approximately <70%.

As used herein, "a reasonable period of time" means the time, ranging from months to years, depending upon the application, a composition may be expected to maintain a safe and efficacious amount of its combined ingredients.

As used herein, "shelf-life stable" and "shelf-life stability" are used interchangeably and refer to the single-phase composition being deemed consumer acceptable after a defined period of time after its production and prior to use (under ambient conditions). The bioavailability and stability of ingredients of single-phase compositions may be determined at any point during their useful shelf-life.

As used herein, "bioavailability" means to the absorption or penetration of the active agent(s) of the composition into the organic matter to which it is exposed and/or the absorption rate proportion of the dose of the composition that reaches the systemic circulation of the organic matter for which its use is intend. For example, when a composition is administered intravenously, its bioavailability is nearly 100%, while when the composition is administered topically, a fraction of the total composition reaches systemic circulation. Some embodiments described herein provide enhanced penetration or absorption of oxidative compounds when applied topically to organic matter. The term "bioavailability" also refers to its availability for efficacy at the desired site and for efficacy that either intracellular, extracellular or within biofluids/biological fluids.

As used herein, "aliphatic anionic compounds" means aliphatic compounds comprising anionic moiety that exhibit surface active properties, ionic interactions with other compounds, physical interaction, etc. as a result of combined physico-chemical properties of aliphatic and anionic structural moieties.

As used herein, "oxidative compounds" mean compounds exhibiting oxidation reaction of biomolecules such as organic acids, amino acids, sulfur compounds, precursors of sulfur compounds, proteins, enzymes etc.

As used herein, "biocidal", "bactericidal", "fungicidal" or synonymous terms mean the property of inactivating or killing microorganisms, such as bacteria, algae, yeast, and fungi. As used herein, "biocidal" also refers to the effect of a composition as a treatment for reduction of bacterial or fungal or microbial growth or overgrowth in fluids or biofilm which may be associated with alleviating a diseased condition or state.

As used herein, "biostatic", "bacteriostatic", fungistatic" or synonymous terms mean the property of arresting the growth of microorganisms, such as bacteria, algae, yeast and fungi. As used herein, "biostatic" means to the effect of a composition in maintaining the polymicrobial mixture of a fluid or a biofilm, as in maintaining the oral ecology so that one or more organisms have not overgrown to enable inflection and disease. Compositions with biostatic attributes are useful in health maintenance, wellness and prevention of infection and disease.

As used herein, "stabilized source of chlorine dioxide," means an aqueous solution comprised of sodium chlorite, potassium chlorite or another chlorite ion source and a compound or compounds intended to inhibit or slow the degradation of the chlorite or chlorite ion source prior to use.

As used herein, "stabilized chlorine dioxide" is a term that is interchangeable with stabilized source of chlorine dioxide. An example of a solution with a stabilized source of chlorine dioxide would be an aqueous solution comprised of sodium chlorite and a buffering system as defined herein.

As used herein, the word "comprise" means the presence of an element without excluding the presence of additional elements. When a composition is comprised of an element, certain advantages of the invention arise from the features specified of the element (and not from unspecified features).

As used herein, a "biofilm" means a biological aggregate that forms a layer on a surface, the aggregate comprising a community of microorganisms embedded in an extracellular matrix of polymers and/or other biocompounds such as glycoproteins. Typically, a biofilm comprises a diverse community of microorganisms, including bacteria (aerobic and anaerobic), algae, protozoa, yeast, and fungi. While mono-species biofilms also exist outside the oral and nasal cavities, biofilms in vivo become polymicrobial as they develop overtime creating oxygen-scare environments where anaerobic pathogens thrive and where the biofilm matrix protects the polymicrobial mixture within from antimicrobial treatment. Pathogens residing in biofilms comprised of polymicrobial mixtures are known to be significantly less susceptible to antimicrobial treatments than those in their planktonic state or those resident in mono-species biofilms created in vitro.

As used herein, "buffering system" means a system containing two or more agents characterized as an acid and its conjugate base or vice versa. Suitable components of buffering system may include carbonates, borates, phosphates, imidazole, citrates, acetates and mixtures thereof, and further may include any of monosodium phosphate, disodium phosphate, trisodium phosphate, alkali metal carbonate salts, imidazole, pyrophosphate salts, acetic acid, sodium acetate, citric acid, and sodium citrate. Exemplary compounds used in generating buffering system are described in more detail in Kirk & Othmer, Encyclopedia of Chemical Technology, Fourth Edition, Volume 18, Wiley-Interscience Publishers (1996).

As used herein, "pH modifying agent" means an agent capable of modifying the pH of a composition. pH modifying agents comprise acidifying agents to lower pH, basifying agents to raise pH and buffering agents to control pH within a desired range. Use or presence of single pH modifying agent does not result in a buffered composition.

As used herein "a carrier" means those components of a composition that are capable of being commingled to provide required physical consistency and consumer goodness properties without interaction with other ingredients.

As used herein, "orally acceptable carrier" means a suitable vehicle or ingredient, which can be used to form and/or apply the present compositions to the oral cavity in a safe and effective manner. Orally acceptable carrier(s) provide consumer goodness properties.

As used herein, "compatible" means that the components of the composition are capable of being commingled without interaction in any manner which would maintain the stability of the oxidative compounds, the ingredients required for the efficacy, the carrier and excipients, and the consumer qualities of the composition.

As used herein, "consumer goodness qualities" include, but are not limited to, appearance, viscosity, taste, odor, abrasiveness, color, flavor, and moisturizing attributes of the compositions deemed desirable by consumers through consumer product testing or other such means. For example, it may be desirable that a tube of toothpaste produce a ribbon stripe of toothpaste on a toothbrush when squeezed and that the toothpaste composition is neither too firm to be squeezed easily from the tube nor too viscous so as not to hold or rest on the toothbrush ready or use. Consumer goodness qualities are known to influence use of oral care products and compliance with oral hygiene practices.

As used herein, "dental plaque" means a polymicrobial biofilm that forms on the surface of teeth. Dental plaque refers to only oral biofilms adherent to teeth. Other biofilms with varying polymicrobial mixtures are found on other surfaces of the oral cavity, such as tongue, cheek, and gums, as well as dental appliances, such as dental implants, bridges, and crowns.

As used herein, "single-phase composition" means a composition wherein all the ingredients are comprised at the time of manufacture into a single composition and do not require mixing or adding of ingredients at the time of use. Further, ingredients in single-phase composition do not separate or phase out on standing or storage. A single-phase composition is preferred due to the simplicity of use by user in commercial goods, the simplicity of packaging as dual-chambered containers or multi-containers are not required for the manufacture, transport, storage and use of the composition.

As used herein, "dual-phase composition" means a composition wherein certain ingredients are contained in one part and other ingredients are contained separately in a second part at the time of manufacture and wherein these parts are stored or packaged separately prior to use to prevent the reactivity of the oxidative compounds to the carrier and other excipients of the composition. The bio-availability of dual phase compositions may be determined once the two phases are mixed at the time of use. A difference between single-phase and dual phase compositions may include how shelf-life is determined. Because the two phases of a dual phase compositions are combined just prior to usage, the shelf-life stability of dual phase compositions is the short period from the time of mixing just prior to use to the time of use. Dual-phase compositions may not have the required attribute of maintaining stability of components from the time of manufacture to the time of usage precisely because the phases of the composition are not mixed until just prior to usage. Consequently, the shelf-life stability and bio-availability of dual phase compositions comprising oxidative compounds, flavoring agents and flavoring systems, and sweetening agents are not directly comparable to single phase compositions.

As used herein, "essentially free" means a composition which is comprised of very low levels, below detection levels of commonly used analytical methods, of a specific ingredient or compound or molecule. For example, fluoride-free composition will not comprise source of fluoride ion as an ingredient but may contain low levels of fluoride that is present as an impurity in other ingredients.

As used herein, "vehicle" means an orally-acceptable dentifrice vehicle used to prepare a dentifrice composition comprising a water-phase, containing a humectant therein.

As used herein, "dentifrice" means paste, gel, powder, tablets, or liquid formulations, unless otherwise specified, that are used to clean the surfaces of the oral cavity.

As used herein, "toothpaste" means a paste or gel formulations, unless otherwise specified, that are used to clean the surfaces of the oral cavity, for example, teeth. A toothpaste may be considered a single-phase composition, though the a toothpaste may contain solid phase abrasive agents uniformly dispersed throughout forming a homogenous and inseparable composition.

As used herein, "teeth" refers to natural teeth as well as artificial teeth or dental prosthesis.

As used herein, "efficacious amount" means any amount of the agent that may result in a desired biocidal or biostatic or chemical or physiological effect, a desired cosmetic effect, and/or a desired therapeutic biological effect. In one example, an efficacious amount of an agent used for tooth whitening may be an amount that may result in whitening of a tooth with one or more treatments. In another example, an efficacious amount of an agent used for wound treatment is an amount that may result in a statistically significant improvement in wound healing.

As used herein, "film" means a layer of a material having two dimensions substantially larger than the third dimension. A film may be a liquid or a solid material. For some materials, a liquid film can be converted into a solid film by curing, for instance, by evaporation, heating, drying, cross-linking, adhering, adduct formation, and like phenomena.

As used herein, "hard tissue" means any toe and finger nail, hard keratinized tissue, hard tooth tissue, bone, tooth and the like, found in animals such as mammals.

As used herein, "irritating" and "irritation" refer to the property of causing a local inflammatory response, such as reddening, swelling, itching, burning, or blistering, by immediate, prolonged, or repeated contact. For example, inflammation of a non-oral mucosal or dermal tissue in a mammal can be an indication of irritation to that tissue. A composition may be deemed "substantially non-irritating" or "not substantially irritating," if the composition is judged to be slightly or not irritating using any standard method for assessing dermal or mucosal irritation.

As used herein, "pharmaceutically acceptable" is set forth broadly and refers without limitation to those compounds, materials, compositions and/or dosage forms which are, within the scope of sound medical judgment suitable for contact with the tissues of and/or for consumption by human beings and animals without excessive toxicity, irritation, allergic response, or other problem complications commensurate with a reasonable risk/benefit ratio.

As used herein, the abbreviation "ppm" means parts per million by weight or volume as applicable.

As used herein, "overgrowth" refers to excessive concentrations of bacteria, algae, yeast, and/or fungi leading to conditions of inflammation, infection, pathogenesis and disease. Overgrowth may occur in biofilms and plaques containing polymicrobial mixtures of bacteria, algae, yeast, and/or fungi, such as those found in the biofilms associated with mucositis and with dental plaque. Overgrowths of pathogenic microbes within polymicrobial biofilms are known to increase significantly their resistance to treatment and increase the incidence of inflamed tissues, infection and disease than those in mono-species biofilms.

As used herein, "prophylactic" means treatment administered to a subject who does not exhibit signs of a disease or exhibits early signs of the disease for the purpose of decreasing the risk of developing pathology associated with the disease.

As used herein, "range" means the area of variation between upper and lower limits on a particular scale. It is understood that any and all whole or partial integers between any ranges set forth herein are included herein.

As used herein, "safe and effective amount" and similar terms mean an amount of an ingredient, such as the amount of an oxidative compound, in composition of sufficient dosage to positively modify the condition to be treated, but low enough to be safe for humans and animals to use without serious side effects (at a reasonable benefit/risk ratio), within the scope of sound medical/dental judgment. "Safe and effective" pertains not only to the dosage amount but also the dosage rate (rate of release) of the oxidative compound applied in treatment. The safe and effective amount of oxidative compound in a composition may vary with the particular condition being treated, the age and physical condition of the patient being treated, the severity of the condition, the duration of treatment, the nature of concurrent therapy, the specific form (e.g., salt) of the oxidative compound employed, and the particular vehicle from which the oxidative compound is applied.

As used herein, a "single-phase composition" means a composition wherein all ingredients are composed in a single container at the time of composing and are not mixed with other ingredients subsequently. Thus, single-phase compositions are ready for use at any time during their shelf-life without further preparation or mixing.

As used herein, "stability" means the prevention of a reaction, reduction or degradation of components, such as of oxidative compounds or flavoring agents and systems, comprised in a single-phase composition. A single-phase composition may be "stable" if the oxidative compounds of the single-phase composition are not reactive with each other for a reasonable period of time. For example, a single-phase composition may stable if it maintains consumer qualities and exhibits less than 35% loss of the oxidative compounds for a period of 24 months at about 25° C. (ambient temperature) or 6 months at an accelerated temperature of 40°±2° C. and 75%±5% Relative Humidity (RH).

As used herein, "shelf-life" means the length of time compositions maintain the desired stability of the oxidative compounds and the consumer qualities of the composition. For example, a target or stable shelf life for a composition may not comprise more than 35% loss in the concentration of oxidative compound in 6 months at 40±2° C. and 75%±5% RH, which is equivalent to 2 years of shelf life at room temperature.

As used herein, "therapeutic" means intended to be administered to a subject who exhibits signs of pathology for the purpose of diminishing or eliminating those signs.

As used herein, "topical composition" means a product which is not intentionally ingested or otherwise applied without recovery for purposes of systemic administration of therapeutic agents, but is retained in the anal, aural, oral, nasal, ocular, or urogenital cavities or upon the skin or other outer surfaces of the body, or upon an area of affected soft tissue for a time sufficient to contact substantially all of the surfaces and/or tissues for purposes of administration and delivery of therapeutic agents.

As used herein, "wound" means a laceration, abrasion, puncture, burn, and/or other injury to any one or more soft and/or hard tissue. Exemplary tissues considered for such wound treatment include mucosal tissue and dermal tissue including epidermal tissue, dermal tissue, and subcutaneous tissue (also called hypodermis tissue). As used herein, a wound also encompasses a laceration, a puncture, and/or an avulsion of a fingernail or toenail. A wound can penetrate the tissue partially or completely. A wound can arise accidently or intentionally, e.g., a surgical wound.

As used herein, "dispersing agent" means a compound that improves the separation of particles and prevents settling or clumping of an ingredient(s) in a multicomponent composition.

As used herein, "emollient agent" means a compound that reduces the loss of water from a composition.

As used herein, "suspending or emulsifying agent" means a compound that achieves uniform dispersion of an ingredient(s) in a multicomponent composition.

As used herein, "fragrance" means a compound that provides a pleasing scent or order similar to perfume to a composition.

As used herein, "cooling agent" means a compound that provides a cooling, soothing, or pleasant feeling when a composition is topically applied to hard and soft tissues.

As used herein, "warming agent" means a compound that provide an olfactory sensation, especially warm sensation. Warming agents are often desired in various cosmetic preparations, such as shaving creams, hand lotions, body lotions, facial preparations, including masks, depilatories.

As used herein, "humectant" means a compound that preserves moisture in a composition. Some embodiments described herein include one or more compounds such as cellulose gum, carboxymethylcellulose, pectin, guar gum, xanthan gum, N-acyl sarcosinate, sodium lauroyl sarcosinate, sodium cocoyl sarcosinate, or sodium myristoyl sarcosinate.

As used herein, "thickener" means a compound that decreases viscosity of a composition.

As used herein, "excipient" means a compound that provides physical and consumer goodness properties to a composition for its acceptance. Examples of such properties (but not limited to) are viscosity, appearance, flavor, color, thickness, sweetness, gel like structure, preservative, uniform suspension or combinations thereof.

As used herein, the term "abrasive agent" means a compound that helps to remove coating (or deposits) from hard or soft tissues, such as that on a tooth surface while brushing using a composition, such as a toothpaste.

As used herein, "desensitizing agent" means a compound that helps reduce or alleviate sensitivity and pain. For example, a desensitizing agent in a topical resin, varnish, toothpaste or mouthwash may occlude dentin tubules or may desensitize nerve fibers, blocking the neural transmission.

As used herein, the term "fluoride-free" means when the source of fluoride ion source in a composition is 0%, is below detection level, does not contain source of fluoride ion as an ingredient or when the composition is essentially free of fluoride.

As used herein, the term "phase stability" may refer to a composition visually (i.e., to the unaided eye) having no liquid separation from the composition's body over a defined period of time under ambient conditions.

All percentages and ratios used herein are by weight of a single-phase composition and not of the overall topical formulation that is delivered, unless otherwise specified. All measurements are made at room temperature i.e. 20-25° C., unless otherwise specified. The concentration of a dissolved oxidative compound may depend on the temperatures and the range of humidity to which the solution is likely to be subjected. Heat and humidity, under normal circumstances, may cause such a composition to degrade from liquid to gas, changing its weight and rendering common assay calculations inaccurate.

Detailed Description of the Embodiments

In various aspects, the single-phase composition comprises an oxidative compound. In embodiments, an oxidizing compound is comprised of at least one of the following: a low-molecular-weight compound, a compound of suitable size and properties to permit diffusion or uptake through the cell wall to react with internal cell components, and a compound which stimulates apoptotic or necrotic cell death. In further embodiments, the oxidative compound is comprised of compounds having a low oxidizing threshold, indicating that the selected oxidative compounds interact strongly with its target by chemical rather than physical means. In further embodiments, the oxidative compound comprises, at least one of, chlorine dioxide or a chlorite ion source, such as stabilized source of chlorine dioxide, a chlorite salt, ammonium peroxydisulfate, carbamide (urea) peroxide, ferric chloride, hydrogen peroxide, potassium bromate, potassium chlorate, potassium perchlorate, potassium dichromate, potassium ferricyanide, potassium peroxymonosulfate, potassium persulfate, sodium bromate, sodium chlorate, sodium perchlorate, sodium chlorite, sodium hypochlorite, sodium iodate, sodium perborate, sodium percarbonate, sodium persulfate, strontium peroxide, zinc acetate, zinc peroxide, zinc chloride or the like.

In further embodiments, a single-phase composition may comprise from about 0.005% to about 8.0% oxidative compound, such as a chlorite ion sources and/or stabilized source of chlorine dioxide. In further embodiments, the single-phase composition may include from about 0.005% to about 4.0% oxidative compound. In further embodiment, the single-phase composition may include from about 0.005% to about 3.0% oxidative compound.

In another embodiment, the single-phase composition is comprised of about 0.005% to about 2.0% oxidative compound.

In certain aspects, the single-phase composition comprises N-acyl sarcosinate. N-acyl sarcosinate may include lauroyl sarcosinate, cocoyl sarcosinate, myristoyl sarcosinate, oleoyl sarcosinate, stearoyl sarcosinate and other such compounds identifiable to a person skilled in the art. In various embodiments, N-acyl sarcosinate is provided in the form of a salt or a pharmaceutically accepted salt, such as, sodium lauroyl sarcosinate, sodium lauryl sulfoacetate, sodium lauryl isethionate, sodium laureth carboxylate, sodium cocoyl sarcosinate, and sodium myristoyl sarcosinate.

In further embodiments, a single-phase composition is provided, comprising from about 0.001% to about 20.0% N-acyl sarcosinate. In further embodiments, the single-phase composition is comprised of about 0.001% to about 10% of N-acyl sarcosinate. In further embodiments, the single-phase composition may be comprised of from about 0.001% to about 5.0% of N-acyl sarcosinate. In further embodiments, the single-phase composition is comprised of about 0.001% to 1% of N-acyl sarcosinate. In further embodiments, the single-phase composition is comprised of from about 0.01% to 1% of N-acyl sarcosinate. In further embodiments, the single-phase composition is comprised of from about 0.01% to 5% of N-acyl sarcosinate.

In further embodiments, the single-phase composition is comprised of from about 0.2% to 5% of N-acyl sarcosinate.

In further embodiments, the single-phase composition comprises from about 0.5% to about 5% of N-acyl sarcosinate.

In certain aspects, the single-phase composition is comprised of a carrier. In embodiments, suitable carrier(s) comprise those that satisfy various considerations based on compatibility with the other ingredients required for the efficacy, consumer qualities, cost, and contribution to shelf stability. In embodiments, the selected carrier does not substantially reduce either the stability of the composition or its efficacy. Examples of suitable carriers variously comprise gelling agents, whitening agents, flavoring agents and flavoring systems, coloring agents, abrasive agents, foaming agents, desensitizing agents, dispersants, humectants, sweetening agents analgesic and anesthetic agents, anti-inflammatory agents, anti-malodor agents, anti-microbial agents, anti-plaque agents, anti-viral agents, biofilm disrupting, dissipating or inhibiting agents, cellular redox modifiers, antioxidants, cytokine receptor antagonists, dental anti-calculus agents, fluoride ion sources, hormones, metalloproteinase inhibitors, enzymes, immune-stimulatory agents, lipopolysaccharide complexing agents, tissue growth factors, vitamins and minerals, water, and mixtures thereof.

In aspects, the single-phase composition is comprised of a buffering system. The buffering system may be required to achieve and maintain a pH of the single-phase composition in the range required to prevent the degradation of the oxidative compound in the single-phase composition. Further, a buffering system may be required to achieve and maintain a pH composition suitable to treating or preventing anal, aural, oral, nasal, ocular, urogenital, foot, and skin disorders, or diseases of the skin or foot and the inflammation and infection of tissues therein. A buffering system may also be useful to achieve consumer goodness properties. In embodiments, the buffering system is comprised of an acid and its conjugate base or a base and its conjugate acid. In embodiments, the buffering system is comprised of an organic acid and its conjugate base or an organic base and its conjugate acid. In some embodiments, the buffering system is comprised of an inorganic acid and its conjugate base or an inorganic base and its conjugate acid. In embodiments, the buffering system is comprised of an organic acid and an inorganic base or an inorganic acid and an organic base. In embodiments, the buffering system maintains a composition pH at a range from about 6.0 to about 8.5. A buffering system generally differs from a single pH modifying agent used to reduce the pH of a composition or raise the pH of a composition in that, while it may be used to raise or lower pH to desired level during comprising the composition, it is also useful to maintain the shelf-life stability and bioavailability of ingredients for a reasonable period of time, as defined herein.

In embodiments, a buffering system is comprised of from about 0.2% to about 4.0%, from about 0.05% to about 0.5%, from about 0.2% to about 2.0%, or from about 0.7% to about 4.2%, or from about 0.7% to about 2.2% of a base compound. In various embodiments, the buffering system is comprised of from about 0.01% to about 4.0%, from about 0.01% to about 0.10%, from about 0.01% to about 0.05%, from about 0.01% to about 0.05%, from about 0.04% to about 2.1% or from about 0.05% to about 2.2%, from about 0.06% to about 0.2%, from about 0.00% to about 0.1% of an acidic compound.

In aspects, the single-phase composition is comprised of two pH modifying agents. pH modifying agents for use herein may comprised of acidifying agents to lower pH, basifying agents to raise pH. For example, one or more compounds can provide a pH from about 2 to about 10, or from about 2 to about 8, or from about 3 to about 9, or from about 4 to about 8, or from about 5 to about 7, or from about 6 to about 10, or from about 6 to about 8, or from about 7 to about 8, or from about 7 to about 9, and any pH above or below this range or any fractional range in between. Orally acceptable pH modifying agents may comprise without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, disodium phosphate, trisodium phosphate, pyrophosphate salts, etc.), imidazole and mixtures thereof. Two pH modifying agents are optionally present in a total amount effective to adjust the composition to an orally acceptable pH range.

In some embodiments, the single-phase composition is comprised of about 0.01% to about 10% pH modifier agents based on a total weight of the oral care composition. In some embodiments, the pH modifier agents are comprised of an amount from about 0.01%, 0.1%, 1%, 2%, 3%, 4%, 5%, 6%, 7%, 8%, 9% to about 10% by weight or volume of the single-phase composition. In other embodiments, a pharmaceutically acceptable carrier is comprised of in an amount from about 0.01% to about 5%, from about 0.01% to about 3%, or from about 0.01% to about 2%. Use or presence of single pH modifying agent generally does not result a buffered composition.

In some aspects, the single-phase composition further is comprised of one or more additional active ingredients. In some embodiments, an additional active ingredient is comprised of one or more of the following additional ingredients: fluoride ion sources, anti-microbial agents, analgesic compounds, anti-inflammatory agents, anti-malodor agents, anti-plaque agents, anti-viral agent, biofilm disrupting, dissipation or inhibiting agents, hormones, enzymes, metalloproteinase inhibitors, immune-stimulatory agents, and numbing agents. In further embodiments, the single-phase composition is comprised of one or more excipients including any of water, abrasives, humectants, thickeners, sweeteners, moisturizers, flavors, colors, fillers, and extenders.

In some aspects, the single-phase composition is comprised of a pharmaceutically acceptable carrier and/or excipients. Pharmaceutically-acceptable carriers comprise one or more compatible solid or liquid materials, including diluents or encapsulating substances, which are suitable for topical administration to the human or animal body and provide physical action or consumer-goodness characteristics acceptable to the user. The pharmaceutical carriers and/or excipients may be combined with the oxidative compounds in a single-phase multi-component composition without interaction in any manner that would reduce the stability of the oxidative compound, the flavoring system, the consumer goodness qualities, the safety and effectiveness of the composition in treating or preventing anal, aural, oral, nasal, ocular, urogenital, foot, and skin disorders, or diseases of the skin or foot and the inflammation and infection of tissues therein. The choice of a pharmaceutically acceptable carrier and/or excipient may be determined by the way the composition is to be introduced into the anal, aural, oral, nasal, ocular, or urogenital cavity, or to be applied topically in foot care and skin care. The pharmaceutically acceptable carrier and/or excipient may depend on secondary considerations such as, but not limited to, consumer goodness qualities, the flavoring system, the buffering system, costs and shelf-life stability.

In embodiments, the pharmaceutically acceptable carrier and/or excipients is comprised of an amount of from about 0.01% to about 30%, for example, from about 0.01%, 0.1%, 1%, 2%, 3%, 4%, 5%, 6%, 7%, 8%, 9% to about 10% by weight or volume of the single-phase composition. In other embodiments, the pharmaceutically acceptable carrier is comprised of an amount from about 0.01% to about 60%, from about 0.01% to about 30%, or from about 0.01% to about 20%.

In aspects, the single-phase composition further is comprised of an abrasive agent. Abrasives are useful as carriers of the single-phase compositions intended for specific oral and dermal applications and uses. For example, abrasive materials provide physical abrasion between toothbrush and teeth to clean pellicle, cuticle, biofilm, plaque, stain, and calculus, while also contributing to the structure of an embodiment and maintaining stability of the overall formulation. In certain dermal embodiments, it may be desirable for the composition to assist in the exfoliation of skin tissues. In some embodiments, the abrasive material is selected from a composition that does not excessively abrade skin, enamel, dentin, or other hard or soft tissues. In embodiments, the abrasive agent comprises, for example, silicas, hydrated silicas, including gels and precipitates; insoluble sodium polymetaphosphate; hydrated alumina; calcium carbonate; calcium hydrogen orthophosphate dihydrate (known in the trade as "dicalcium phosphate"); tricalcium phosphate, calcium polymetaphosphate, sodium bicarbonate and resinous abrasive materials. In some embodiments, a mixture of abrasives may also be used.

In embodiments, the abrasive is comprised of an amount from about 0.01% to about 70%, for example, from about 0.01%, 0.1%, 1%, 2%, 5%, 10%, 15%, 20%, 30%, 40%, 50% to about 70% by weight of the single-phase composition. In some embodiments, the abrasive agent is comprised of an amount from about 6% to about 70%, from about 10% to about 50%, or from about 6% to about 70%, from about 20% to about 70%. In some embodiments, such as nasal or oral sprays, oral or vaginal rinses and non-abrasive gel compositions, such as those used in wound healing, is comprised of no abrasive.

In aspects, the single-phase composition is comprised of an alkali metal bicarbonate salt. Alkali metal bicarbonate salts are soluble in water and, unless stabilized, tend to degrade oxidative compounds in an aqueous system. Sodium bicarbonate, also known as baking soda, may be comprised as an alkali metal bicarbonate salt into the single-phase composition. In embodiments, the alkali metal bicarbonate salt is comprised of an amount of from about 0.01% to about 70%, for example, from about 0.01%, 0.1%, 1%, 5%, 10%, 20%, 30%, 40%, 50%, 60%, to about 70% by weight of the single-phase composition. In some other embodiments, the alkali metal bicarbonate salt is comprised of an amount from about 0.5% to about 70%, from about 1% to about 50%, or from about 5% to about 50%.

In aspects, the single-phase composition further is comprised of additional agents which reduce dental plaque, tartar and calculus from teeth. In embodiments, the additional agents comprise zinc ions, a cationic material, such as guanides and quaternary ammonium compounds, as well as non-cationic compounds such as halogenated salicylanilides. In some embodiments, an anti-calculus agent is provided, and is comprised of a pyrophosphate ion source, such as pyrophosphate salts. The pyrophosphate salts comprised in the single-phase composition may include di-alkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may be used. In certain embodiments, the pyrophosphate salt is comprised of in one of three ways: predominately dissolved, predominantly undissolved, or a mixture of dissolved and undissolved pyrophosphate. In certain embodiments, the single-phase composition is comprised of a mixture of dissolved and undissolved pyrophosphate salts. Polyolefin phosphates comprise those wherein the olefin group contains 2 or more carbon atoms. Other useful materials comprise synthetic anionic polymers, including poly-acrylates and copolymers of maleic anhydride or acid and methyl vinyl ether (e.g., Gantrez®), as well as, e.g., polyamino propane sulfonic acid (AMPS), zinc citrate trihydrate, poly-phosphates (e.g., tripolyphosphate; hexametaphosphate), diphosphonates (e.g., EHDP; AHP), polypeptides (such as polyaspartic and polyglutamic acids), and mixtures thereof.

In embodiments, the anti-calculus agent is comprised of an amount of from about 0.01% to about 50%, for example, from about 0.01%, 0.1%, 1%, 5%, 10%, 15%, 20%, 25%, 30%, 40%, or to about 50% by weight of the single-phase composition. In other embodiments, the anti-calculus agent is comprised of an amount from about 0.5% to about 25%, from about 1% to about 25%, or from about 5% to about 50%.

In aspects, a single-phase composition is comprised of a coloring agent. Coloring enables the consumer to more readily ascertain usage and dosage. Certain colors of the composition may be deemed undesirable for certain anal, aural, ocular, oral or urogenital applications. In embodiments, a coloring agent is comprised of, FD&C Blue No. 1 or titanium dioxide. Suitable coloring agents are comprised of those that are stable and do not degrade in the presence of the oxidative compounds and do not degrade oxidative compounds. In certain embodiments, the coloring agent is comprised of an amount of from about 0.01% to about 10%, for example, from about 0.01%, 0.1%, 1%, 2%, 3%, 4%, 5%, 6%, 7%, 8%, to about 10% by weight or volume of the single-phase composition. In other embodiments, the coloring agent is comprised of an amount from about 0.5% to about 10%, from about 1% to about 10%, or from about 0.01% to about 2%, or from 0.8% to about 1.1%. Selection of coloring agents and their concentration is made to achieve consumer goodness qualities of the particular embodiment of the composition.

In aspects, a single-phase composition is comprised of a cooling and/or warming agent. Suitable cooling and/or warming agents may be those that are stable and do not degrade the presence of the oxidative compound within the compositions, such as those described in U.S. 2017/0877199 to Patton.

In aspects, the single-phase composition is comprised of a flavoring agent and/or flavoring systems. Suitable flavoring agents are comprised of those that are stable and do not degrade in the presence of the oxidative compounds and do not degrade oxidative compounds. Suitable flavoring systems is comprised of an emulsified flavoring agent for protecting the flavoring agent from degradation. Suitable flavoring systems comprise those that are taught by U.S. 2012/0164084. In some embodiments, a flavoring agent comprises menthol, mint oil, emulsified mint oil, bubblegum flavor, watermelon flavor or different types of berry flavor. In embodiments, the flavoring agent may be present in an amount of from about 0.01% to about 10%, for example, from about 0.01%, 0.1%, 1%, 2%, 3%, 4%, 5%, 6%, 7%, 8%, or to about 10% by weight or volume of the single-phase composition. In some other embodiments, the flavoring agent may be in an amount from about 0.25% to about 1.2%, from about 1.1% to about 10%, or from about 1.1% to about 7.5%.

In aspects, the single-phase composition is comprised of a sweetening agent. Suitable sweetening agents are those that are stable and do not degrade in the presence of oxidative compounds and do not degrade oxidative compounds. In embodiments, the sweetening agent is comprised of sucrose, aspartame, acesulfame, *stevia*, saccharin; saccharin salts, especially sodium saccharin; sucralose, sodium cyclamate, and mixtures thereof. In embodiments, a single-phase composition is essentially free of polyhydroxy sweeteners such as xylitol, mannitol, and sorbitol. In embodiments, a sweetening agent is comprised of sucrose, sucralose, acesulfame, aspartame, cyclamate, or saccharin. In some embodiments, the sweetener is comprised of an amount of from about 0.01% to about 0.5%, for example, from about 0.01%, 0.02%, 0.05%, 0.1%, 0.2%, 0.3%, 0.4%, to about 0.5% by weight or volume of the single-phase composition. In other embodiments, the sweetener is comprised of an amount from about 0.05% to about 0.5%, from about 0.1% to about 0.2%, from about 0.01% to about 0.5%, or from 0.01% to about 0.2%.

In aspects, a single-phase composition further is comprised of one or more humectants. Suitable humectants serve one or more purposes: to keep pastes and gels and suspensions from hardening or losing their consumer goodness qualities when exposed to air, to add to the compositions a moist feel to the consumer goodness qualities and, for particular humectants orally applied, and to impart desirable sweetness of flavor, such as in toothpaste compositions. In embodiments, the humectant is comprised of polyhydroxy alcohols, including arabitol, erythritol, glycerol, maltitol, mannitol, sorbitol, and/or xylitol. Polyhydroxy alcohols are commonly accepted excipients and most belong to the Generally Recognized as Safe (GRAS) category for pharmaceutical, cosmetic, and food products. Other compounds which provide moist texture for suitable formulations may also be used. Humectants such as glycerol, sorbitol and other polyhydroxy compounds have been known to cause degradation of oxidative compounds when comprised in the same single-phase composition. However, in accordance with various aspects, it has been discovered that a single-phase composition being comprised of both an oxidative compound and an aliphatic anionic compound (e.g., an N-acyl sarcosinate compound) can serve as an humectant by providing consistency to the composition and by maintaining the stability of the oxidative compound. In various embodiments, sorbitol functions a humectant comprised in the single-phase composition.

In some embodiments, the humectant is comprised of an amount of about 0.001% to about 70%, for example, from about 0.001%, 0.01%, 1%, 2%, 5%, 10%, 20%, 30%, 40%, 50%, to about 70% by weight or volume of the single-phase composition. In some other embodiments, the humectant may be in an amount from about 1% to about 15%, from about 15% to about 55%, or from about 25% to about 55%.

In aspects, the single-phase composition is comprised of a fluoride ion source. In embodiments, the single-phase composition is comprised of free fluoride ions or covalently bound fluorine in a form that may be hydrolyzed by oral enzymes to yield free fluoride ions. Free fluoride ions are comprised from sodium fluoride, silver diamine fluoride, stannous fluoride, or indium fluoride. Covalently bound fluorine, which can be enzymatically hydrolyzed to yield free fluoride, may be provided by sodium monofluorophosphate. In various embodiments, sodium fluoride is the source of free fluoride ions in the single-phase composition. If a fluoride ion source is used as a component in a single-phase composition, a "fluoride ion source" as disclosed in, U.S. Patent Application Publication No. 2011/0318282 is preferred. Surprisingly, certain embodiments of a single-phase composition comprised of a fluoride ion source will resist significant degradation of the oxidative compound and promote shelf-life and shelf-life stability. In embodiments, a single-phase composition comprises a fluoride ion source, an aliphatic anionic compound (e.g., an N-acyl sarcosinate compound), and an oxidative compound. The composition will remain stable for a reasonable period of time, as defined herein. The composition will maintain the capacity of the oxidative compounds to react or activate upon use. The composition may enhance the capacity of the oxidative compounds to increase penetration of bacteria and biofilms as opposed to comparable compositions not containing an aliphatic anionic compound. In some embodiments, the fluoride ion source is comprised of at least one of indium fluoride, sodium fluoride, silver diamine fluoride, stannous fluoride or sodium monofluorophosphate.

In embodiments, a single-phase composition further is comprised of a source of fluoride ion that yields fluoride ions up to about 5000 ppm, or from about 50 ppm to about 3500 ppm, from about 500 ppm to about 3500 ppm. In some embodiments, the fluoride ion source is comprised of an amount of from about 0% to about 2.0%, for example, from about 0.01%, 0.1%, 0.15%, 0.2%, 0.3%, 0.4%, 0.5%, 0.6%, 0.7%, 0.8%, to about 2.0% by weight or volume of the single-phase composition. In other embodiments, the fluoride ion source is comprised of an amount from about 0.0% to about 0.03%, from about 0.0% to about 0.7%, from about 0.1% to about 0.8%, from about 0.01% to about 0.07%, or from about 0.0% to about 0.8%. In embodiments, a single-phase composition further is fluoride-free as described herein.

In aspects, a single-phase composition further is comprised of a thickening or binding agent. The thickening or binding agent may provide one or more desired consumer goodness qualities appropriate to the single-phase composition, such as the desirable consistency or viscosity of the composition, to provide desirable dosage and to provide a rate of release desired of the oxidative compounds upon use, or to adhere to hard or soft tissues in a topical application. Examples of thickening or binding agents is comprised of carboxyvinyl polymers, seaweed derivatives such as carrageenan, hydroxyethyl cellulose, laponite, powdered polyethylene, and water-soluble salts of cellulose ethers such as sodium carboxymethylcellulose and sodium carboxymethyl hydroxyethyl cellulose. Natural gums such as gum karaya, guar gum, xanthan gum, gum arabic, and gum tragacanth can also be used. Colloidal magnesium aluminum silicate or finely divided silica may be used as part of the thickening or binding agent to further improves texture. Higher concentrations of thickening agents can be used for chewing gums, lozenges (including breath mints), sachets, non-abrasive gels and gels intended for use in wound-healing, vaginal or oral disease.

In some embodiments, the thickening or binding agent is comprised of an amount of from about 0% to about 15%, for example, from about 0.01%, 0.1%, 1%, 2%, 3%, 4%, 5%, 6%, 7%, 8%, or to about 15% by weight or volume of the single-phase composition. In some other embodiments, the thickening or binding agent is comprised of an amount from about 0.1% to about 15%, from about 2.0% to about 10%, from about 4% to about 8%, from about 1.0% to about 4.0%, or from about 5.0% to about 7.0%.

In aspects, the single-phase composition further is comprised of a whitening and/or opacifying agent. In these embodiments, the whitening and/or opacifying agent is comprised of a non-hydrogen peroxide whitening agent. For example, titanium dioxide is comprised of a single-phase composition to achieve whiteness or opaqueness of the composition. In various embodiments, a whitening and/or opacifying agent is comprised of a peroxide, metal chlorite, perborate, percarbonate, peroxyacid, persulfate, and combinations thereof. Suitable peroxide compounds be comprised of hydrogen peroxide, urea peroxide (carbamide peroxide), calcium peroxide, and mixtures thereof. In various embodiments, the single-phase multi-component composition is essentially free of glycerin and/or polyhydroxy compounds. In embodiments, the whitening and/or opacifying agent is comprised of an amount of from about 0% to about 20%, for example, from about 0.01%, 0.1%, 2%, 4%, 6%, 8%, 10%, 12%, 14%, 16%, to about 20% by weight or volume of the single-phase composition. In some other embodiments, the fluoride ion source is comprised of an amount from about 0.01% to about 20%, from about 0.5% to about 10%, or from about 4% to about 7%.

In aspects, the single-phase composition further is comprised of water. Water may provide the remaining weight percent of the single-phase compositions (i.e., the weight percent not attributed to the other components described herein). Water used in the single-phase compositions used as commercially suitable topical compositions can be of low ion content and essentially free of organic impurities. Water is comprised of up to about 98% of the composition, particularly for mouthwashes, mouth rinses and mouthwashes, oral and nasal sprays, vaginal douches, and soaks, and preferably from about 5% to about 60%, by weight of the aqueous compositions herein. These amounts of water comprise the free water which is added to the composition plus that which is introduced with other materials comprising the composition. Some embodiments of single-phase compositions described herein such as powders, lozenges and chewing gum, are of course essentially free of or contain only a small amount of water.

In aspects, the single-phase composition further is comprised of a surfactant. Surfactants may be anionic, cationic, non-ionic, or amphoteric (zwitterionic). These may be useful as foaming agents in oral care, cosmetic, healthcare, and pharmaceutical products. Such foaming agents may also useful in the retention of sanitizing and moisturizing agents in skin care products, such as shaving creams and foams. In certain embodiments, the surfactant is comprised of an amount of from about 0% to about 15%, for example, from about 0.01%, 0.1%, 1%, 2%, 3%, 4%, 5%, 6%, 7%, 8%, to about 15% by weight or volume of the composition. In some other embodiments, the surfactant is comprised of an amount from about 0.1% to about 15%, from about 2.0% to about 10%, or from about 4% to about 8%.

In aspects, the single-phase composition further is comprised of a desensitizing agent. The desensitizing agent may be provided for temporary relief from pain to hard or soft tissues. In certain embodiments, the desensitizing agent is comprised of compounds such as strontium chloride, strontium acetate, arginine, hydroxyapatite, nano-hydroxyapatite (nano-HAp), calcium sodium phosphosilicate, potassium chloride or potassium nitrate. In various embodiments, the compositions is essentially free of compounds that may irritate sensitive body cavities such as anal, nasal, ocular, oral, and urogenital such as sodium lauroyl sulfate.

Examples of sensitivities and resultant diseases oral cavity include canker sores, oral mucositis, and dry mouth.

In aspects, the single-phase composition further is comprised of a preservative. In embodiments, the preservative comprises a methyl paraben, propyl paraben, disodium EDTA, benzyl alcohol, benzoic acid, sodium benzoate or potassium sorbate. In embodiments, the preservative may be present in an amount of from about 0% to about 2%, for example, 0.01%, 0.1%, 1%, or 2% by weight or volume of the composition. In other embodiments, the surfactant may be in an amount from about 0.1% to about 0.15%, from about 0.2% to about 1%, from about 0.01% to 0.5%, or from about 0.4% to about 0.8%.

In various embodiments, the single-phase composition does not contain a polyhydroxy compound. Polyhydroxy compounds are known to react and degrade oxidative compounds and compounds, such as stabilized chlorine dioxide, and therefore, are excluded from these compositions. Polyhydroxy compounds that are not to be used in the composition comprise glycerin, alcohols, polyethylene glycols, xylitol, and sorbitol.

In various embodiments, the single-phase compositions described herein are single-phase compositions. In certain embodiments, the composition is configured to form a dentifrice. In certain embodiments, the composition is configured to form an oral rinse. In other embodiments, the composition is configured to form an oral care composition, such as an oral spray, oral gel, denture or dental appliance soak, toothbrush soak, or a solution intended for use in an oral irrigation device. In certain embodiments, the composition is configured to form a nasal spray. In other embodiments, the composition is configured to form nasal drops or droplets.

In aspects, the single-phase composition is formulated as a cosmetic. Cosmetic compositions (for example, a solid cosmetic composition, such as a gel, soft-solid or semi-solid (cream), or stick), may be comprised of a base composition containing at least one silicone fluid (for example, silicone liquids such as silicone oils) which is thickened using a siloxane-based polyamide as a gelling agent; a carrier in which cosmetically active materials are incorporated; and at least one active ingredient to provide the activity for such cosmetic composition. In embodiments, the cosmetic compositions are transparent (clear), including solid transparent (clear) compositions. In embodiments, the cosmetic composition is formulated that the final composition is opaque. In embodiments, the cosmetic composition is formulated so that the final composition is not-transparent.

In various embodiments, the cosmetic is comprised of one or more additional agents as carriers, selected from one or more of abrasive polishing materials, alkali metal bicarbonate salts, analgesic and anesthetic agents, anti-inflammatory agents, anti-malodor agents, anti-microbial agents, anti-plaque agents, and anti-viral agents, biofilm disrupting, dissipating or inhibiting agents, buffers and buffering systems, cellular redox modifiers and antioxidants, coloring agents and coloring systems, cytokine receptor antagonists, dental anti-calculus agents, hormones, metalloproteinase inhibitors, immune-stimulatory agents, lipopolysaccharide complexing agents, tissue growth factors, titanium dioxide, vitamins and minerals, and mixtures thereof. In certain embodiments, it is commonly understood that combinations of some agents in the same delivery system, may be useful to obtain an optimal effect. In some embodiments, the single-phase composition is comprised of one or more such agents in a single-phase delivery system to provide combined effectiveness, while maintaining the stability of the oxidative compound (e.g., stabilized source of chlorine dioxide).

In various embodiments, the single-phase composition may be specifically formulated for use in humans or for use in other animals, for example in the form of rinses, gels, pastes, creams, washes, sprays, lozenges, therapeutic floss, tape, patches, compresses, or strips, for use in skin care, oral care, urogenital care, foot care, wound healing and as a solution used in irrigation devices for use in the oral and other body cavities. These embodiments may vary, for example, when formulated for humans and when formulated for horses and dogs.

In aspects, the single-phase composition has specific consumer goodness qualities. In embodiments, ingredients are selected for an oral care composition that achieves a desirable range of viscosity to ensure product manufacturability, applicability, stability, and quality, as well as consumer acceptance. In embodiments, the single-phase composition may be phase stable as defined herein. Such phase stable single-phase compositions may resist syneresis. For example, a toothpaste embodiment as taught herein may be less abrasive on teeth than a similar composition without the inclusion of aliphatic anionic compounds. In a liquid embodiment, such as an oral rinse, consumer goodness qualities may be comprised so that the composition retains clarity (transparent composition). In another embodiment, a vaginal douche embodiment may require consumer goodness characteristic that it does not sting, stain, burn or otherwise cause irritation to the user, has a viscosity that enables ease of use, and has a pleasing fragrance or no fragrance at all. Consumer goodness qualities of various embodiments herein may vary for use with other animals. For example, an oral rinse for dogs may have preferably a meat flavor while one for humans may have a mint flavor.

In aspects, the single-phase composition is suitable for a variety of indications, including treatment and prevention of oral or vaginal malodor, as well as ocular, nasal and skin care and other topical uses. Suitable topical indications comprise anal, aural, oral, nasal, ocular, urogenital, foot-care and skin-care conditions and diseases. The composition may be suitable for select indications, including antimicrobial, antiseptic, antioxidant, bactericidal and bacteriostatic, biofilm penetration, biofilm dissipation and reduction, coagulant, deodorant, desensitizing, disinfectant, fungicidal and fungistatic, herbicidal, tissue damage reduction, bleaching, stain removal, and tooth whitening. Compositions herein are suitable for use in a variety of forms, including rinses, gels, pastes, creams, washes, sprays, lozenges, floss, tape, patches, bandages, compresses, wraps, and strips.

In aspects, the single-phase composition maintains stability and consumer goodness. In embodiments, stability and consumer goodness are maintained from the time of manufacture of the composition through about twelve (12) months of storage under ambient conditions. In embodiments, the composition may exhibit no more than 10% loss in stabilized chlorine dioxide in three (3) months at 40±2° C. and 75%±5% relative humidity (RH) which may be equivalent to twelve (12) months of storage at room temperature. In embodiments, the composition may exhibit no more than 20% loss in stabilized chlorine dioxide in three (3) months at 40±2° C. and 75%±5% relative humidity (RH). In embodiments, the composition may exhibit no more than 30% loss in stabilized chlorine dioxide in three (3) months at 40±2° C. and 75%±5% relative humidity (RH). In some embodiments, the composition may exhibit no more than 40% loss in stabilized chlorine dioxide in three (3) months at 40±2° C. and 75%±5% relative humidity (RH) In another embodiment, storage of the composition under accelerated conditions (typically 40±2° C. and 75%±5% relative humidity, RH) can project real time suitability of the composition for consumer use, anticipating the time of manufacture, transit from point of manufacture to wholesaler, from wholesaler to retailer, from retailer to consumer, plus the anticipated storage time by the consumer as the product is consumed.

In various embodiments, as described herein, the present inventors have unexpectedly discovered that the combined effect of sodium myristoyl sarcosinate and sodium chlorite in a single-phase composition improves the remineralization of teeth (as a combined result of enhanced remineralization and reduced demineralization) that is greater than the combination of sodium lauroyl sarcosinate and sodium chlorite. Moreover, as shown and described herein, in various embodiments, the sodium myristoyl sarcosinate and sodium chlorite combination unexpectedly provides a lower Relative Dentin Abrasivity (RDA) value than the combination of sodium lauroyl sarcosinate and sodium chlorite.

Examples of Compositions of the Invention and Testing of Composition

Various embodiments of the composition taught herein are presented below, and testing of those embodiments is presented to demonstrate the various aspects of the novelty of the invention.

Exemplary Composition I: Toothpaste Embodiment

Various single-phase oral care toothpaste compositions are comprised of: from about 0.005% to about 2.0% a chlorite ion source such as sodium chlorite, from about 0.7% to about 4.2% a base such as disodium hydrogen phosphate or trisodium phosphate, from about 0.05% to about 2.20% an acid or a buffering salt on the acidic side, such as sodium dihydrogen phosphate, citric acid, or acetic acid, from about 0.2% to about 5.0% an N-acyl sarcosinate compound, such as sodium lauroyl sarcosinate, sodium cocoyl sarcosinate, or sodium myristoyl sarcosinate, from about 0.8% to about 1.1% coloring agent such as FD&C Blue No. 1 or titanium dioxide, from about 1.0% to about 4.0% gelling agent such as gelatin, pectin, guar gum, xanthan gum, other natural or synthesized gums, cellulose gum or sodium carboxymethyl cellulose, from about 20.0% to about 70.0% abrasive agent such as hydrated silica, calcium hydrogen phosphate, alumina, sodium bicarbonate, from about 0.05% to about 0.5% sweetening agent such as sucrose, sucralose, acesulfame, aspartame, cyclamate, or saccharin, from about 0.025% to about 1.2% flavoring agent such as menthol, mint oil, emulsified mint oil, tropical fruit, watermelon, bubblegum, strawberry or berry flavor, from about 0.0% to about 0.8% fluoride ion source or source of releasable fluoride ion, such as sodium fluoride, silver diamine fluoride, sodium monofluorophosphate, or stannous fluoride, and water to 100%, thereby maintaining the final pH in the range of about 6.0 to about 8.0. For preparing fluoride-free toothpaste compositions, the fluoride ion source is eliminated from the composition and the quantity of water is adjusted accordingly.

Exemplary Composition II: Oral Care Gel Embodiment

Various single-phase oral care gel compositions are comprised of: from about 0.005% to about 2.0% chlorite ion source such as sodium chlorite, from about 0.7% to about 4.2% a base, such as disodium hydrogen phosphate or trisodium phosphate, from about 0.05% to about 2.20% an acid or a buffering salt on the acidic side, such as phosphoric acid, sodium dihydrogen phosphate, citric acid, or acetic acid, from about 0.2% to about 5.0% an N-acyl sarcosinate compound, such as sodium lauroyl sarcosinate, sodium cocoyl sarcosinate, or sodium myristoyl sarcosinate, from about 5.0% to about 7.0% gelling agent such as gelatin, pectin, xanthan gum, guar gum, cellulose gum, other natural or synthesized gums, or sodium carboxymethyl cellulose, from about 0.05% to about 0.5% sweetening agent such as sucrose, acesulfame, aspartame, sucralose, or saccharin, from about 0.025% to about 1.2% flavoring agent such as menthol, mint oil, emulsified mint oil, bubblegum flavor, strawberry, fruity, watermelon or berry flavor, from about 0.01% to about 0.8% fluoride ion source such as sodium fluoride stannous fluoride, or sodium monofluorophosphate, and water to 100% thereby maintaining the final pH in the range of about 6.0 to about 8.0. For preparing fluoride-free gel compositions, the fluoride ion source is eliminated from the composition and the quantity of water is adjusted accordingly. The compositions are comprised of a buffering system and/or a flavoring system as described herein.

Exemplary Composition III: Oral Rinse Embodiment

Various single-phase oral care rinse compositions are comprised of from about 0.005% to about 2.0% of chlorite ion source such as sodium chlorite, from about 0.2% to about 4.0% a base, such as disodium hydrogen phosphate or trisodium phosphate, from about 0.04% to about 2.10% an acid or a buffering salt on the acidic side, such as sodium dihydrogen phosphate, phosphoric acid, citric acid or acetic acid, from about 0.01% to about 1.0% an N-acyl sarcosinate compound such as sodium lauroyl sarcosinate, sodium cocoyl sarcosinate, or sodium myristoyl sarcosinate, from about 0.01% to about 0.2% sweetening agent such as sucrose, acesulfame, aspartame, cyclamate, sucralose, or saccharin, from about 0.025% to about 1.2% flavoring agent such as menthol, mint oil, emulsified mint oil, tropical fruit, bubblegum, watermelon, strawberry or berry flavor, from about 0.0% to about 0.07% fluoride ion source or source of releasable fluoride ion, such as sodium fluoride, stannous fluoride, sodium monofluorophosphate, or acidulated phosphate fluoride, and water to 100% thereby maintaining the final pH in the range of about 6.0 to about 8.0. For preparing fluoride-free oral rinse compositions, the fluoride ion source is eliminated from the composition and the quantity of water is adjusted accordingly. Similarly, for preparing fluoride-free and unflavored oral rinse compositions, the fluoride ion source and the flavoring agents are eliminated from the composition. The composition may comprise a buffering system and/or a flavoring system as described herein.

Exemplary Composition IV: Oral Spray Embodiment

Various single-phase oral care spray formulation may comprise: from about 0.005% to about 2.0% chlorite ion source such as sodium chlorite, from about 0.05% to about 0.5% a base such as disodium hydrogen phosphate, sodium citrate, or trisodium phosphate, from about 0.01% to about 0.05% an acid or a buffering salt on the acidic side, such as phosphoric acid, citric acid, acetic acid, or sodium dihydrogen phosphate, from about 0.01% to about 1.0% an N-acyl sarcosinate compound such as sodium lauroyl sarcosinate, sodium cocoyl sarcosinate, or sodium myristoyl sarcosinate, from about 0.01% to about 0.5% sweetening agent such as sucrose, acesulfame, aspartame, cyclamate, sucralose, or saccharin, from about 1.1% to about 7.5% flavoring agent such as menthol, mint oil, emulsified mint oil, watermelon, bubblegum, tropical fruit, strawberry or berry flavor, from about 0.5% to 7.0% dispersing agent such as a polysorbate, from 0.01% to 0.5% preservative, such as methyl paraben, propyl paraben, disodium EDTA, sodium benzoate, potassium sorbate, benzoic acid or combination thereof and water to 100% thereby maintaining the final pH in the range of about 6.0 to about 8.0. The compositions are comprised of a buffering system and/or a flavoring system as described herein.

Exemplary Composition V: Nasal Spray Embodiment

Various nasal channel care spray formulations may comprise: from about 0.005% to about 1.0% chlorite salt such as sodium chlorite, from about 0.01% to about 4.0% a base such as disodium hydrogen phosphate, sodium citrate, or trisodium phosphate, from about 0.001% to about 0.4% an acid or a buffering salt on the acidic side, such as phosphoric acid, citric acid, acetic acid, or sodium dihydrogen phosphate, from about 0.05% to 7.0% dispersing agent such as a polysorbate, 0.05% to 5.0% salt such as sodium chloride or potassium chloride, and water to 100% thereby maintaining the final pH in the range of 6.0 to 8.0. Optional ingredients in oral spray embodiments are from 0.0001% to 0.5% preservatives, such as methyl paraben, propyl paraben, disodium EDTA, sodium benzoate, potassium sorbate, benzoic acid or combination thereof, from about 0.001% to about 0.5%, sweetening agents such as sucrose, acesulfame, aspartame, cyclamate, sucralose, or saccharin, and from about 0.05% to about 7.5%, flavoring agents or a flavoring systems comprising flavoring agents, such as menthol, mint oil, emulsified mint oil, watermelon, bubblegum, tropical fruit, strawberry or berry flavor.

In various embodiments, various single-phase nasal spray formulations may comprise from about 0.005% to about 1.0% chlorite ion source such as sodium chlorite, from about 0.01% to about 0.5% a base such as disodium hydrogen phosphate, sodium citrate, or trisodium phosphate, from about 0.01% to about 0.05% an acid or a buffering salt on the acidic side, such as phosphoric acid, citric acid, acetic acid, or sodium dihydrogen phosphate, from about 0.01% to about 1.0% an N-acyl sarcosinate compound such as sodium lauroyl sarcosinate, sodium cocoyl sarcosinate, or sodium myristoyl sarcosinate, from about 0.1% to 5.0% dispersing agent such as a polysorbate, 0.05% to 5.0% salt such as sodium chloride or potassium chloride, from 0.01% to 0.5% preservative, such as methyl paraben, propyl paraben, disodium EDTA, sodium benzoate, potassium sorbate or combination thereof and water to 100% thereby maintaining the final pH in the range of about 6.0 to about 8.0. The compositions are comprised of a buffering system as described herein.

Exemplary Composition VI: Wound-Healing Gel/Ointment Embodiment

Various single-phase oral care gel compositions are comprised of from about 0.005% to about 2.0% chlorite ion source such as sodium chlorite, from about 0.7% to about 2.2% a base such as disodium hydrogen phosphate or trisodium phosphate, from about 0.06% to about 0.20% an acid or a buffering salt on the acidic side, such as sodium dihydrogen phosphate, citric acid, or acetic acid, from about 0.5 to 5.0% an N-acyl sarcosinate compound, such as sodium lauroyl sarcosinate, sodium cocoyl sarcosinate, or sodium myristoyl sarcosinate, from about 5.0% to about 7.0% gelling agent such as gelatin, pectin, guar gum, xanthan gum, cellulose gum, or sodium carboxymethyl cellulose, from about 0.025% to about 1.2% a cooling agent, such as menthol or emulsified mint oil, from about 0.1% to about 10% an emollient agent, such as mineral oil, from about 0.1% to about 5% a suspending or emulsifying agent, such as a polysorbate, and water to 100% thereby maintaining the final pH in the range of about 6.0 to about 8.0. The compositions are comprised of a buffering system and/or a flavoring system as described herein.

Exemplary Composition VII: Vaginal Douche Embodiment

Various single-phase vaginal douche compositions are comprised of from about 0.005% to about 2.0% a chlorite ion source such as sodium chlorite, from about 0.2% to about 2.0% a base such as sodium bicarbonate, disodium hydrogen phosphate or trisodium phosphate, from about 0.00% to about 0.10% an acid or a buffering salt on the acidic side, such as boric acid, citric acid, acetic acid, or sodium dihydrogen phosphate, from about 0.001% to about 1.0% an N-acyl sarcosinate compound such as sodium lauroyl sarcosinate, sodium cocoyl sarcosinate, or sodium myristoyl sarcosinate, from about 0.1% to about 10% an emollient agent, such as mineral oil, from about 0.1% to about 5% a suspending or emulsifying agent, such as a polysorbate or poloxamer, from 0.01% to 20% a fragrance, such as rose, lilac or geranium fragrance, or other proprietary fragrance compositions provided by commercial suppliers of fragrances, and water to 100% thereby maintaining the final pH in the range of about 6.0 to about 8.0. For preparing fragrance-free vaginal douche compositions, the fragrance source is eliminated from the composition and the quantity of water is adjusted accordingly. The compositions are comprised of a buffering system and/or a flavoring system as described herein.

Methods for Preparing Exemplary Compositions I through VII

In preparing compositions as described herein and where the Exemplary Composition is a paste or gel, the gelling agents are dissolved in water. Pharmaceutically-acceptable buffering compounds of the appropriate type and concentration such as weak acid and its conjugate base or weak base and its conjugate acid are then added to the solution of gelling agent in water until the preferred final pH range of 6.0 to 8.5 is achieved. Then the solution containing a buffering system may be mixed with the chlorite ion source in an aqueous solution. The remaining ingredients, e.g. humectants, sweetening agents, coloring agents, abrasive agents, fluoride ion source, flavoring agent(s), emollient agents, suspending or emulsifying agents, additional deionized or purified water, and other ingredients as described above and as applicable, are added one by one in appropriate amounts to maintain the final pH of the overall formulation in the range of 6.0 to 8.5. The N-acyl sarcosinate may be added as a last ingredient while preparing the composition. All compounding may occur at ambient temperatures to maintain the stability of the composition. The composition is then mixed by stirring under vacuum for about 45 mins for removing any trapped air. The vacuum is then released and the composition is dispensed in tubes for use.

Similarly, in preparing a single-phase composition where the Exemplary Composition is a liquid, a rinse or an aerosol spray, the base compound selected may be dissolved in deionize or purified water in a separate preparation. This solution may be mixed with the chlorite ion source in an aqueous solution. The remaining ingredients, e.g. sweetening agents, flavoring agents, fluoride ion source, additional deionized or purified water, and/or other ingredients as described above and as applicable, are added one by one in appropriate amounts. The N-acyl sarcosinate such as sodium lauroyl sarcosinate may be added prior to adding the weak acid while preparing the composition. The appropriate amount of weak acid may be dissolved in water and the appropriate quantity may be mixed with the composition to maintain the final pH of the overall formulation in the range of 6.0 to 8.5. The base compound and the weak acid of the composition constitute the buffering system as defined herein. All compounding may be required to occur at ambient temperatures to maintain the stability of the composition.

The composition is then mixed by stirring for about 45 mins for achieving homogeneity. The composition is then dispensed in tubes for use.

In preparing a single-phase composition where the Exemplary Composition is a liquid spray, the method for preparation follows the method for oral rinse composition taught above, wherein additional ingredients such as dispersing agents, humectants, or preservatives are mixed with the composition prior to adjusting the pH of the final composition in the range of 6.0 to 8.5.

Example 1. Formulations of a Toothpaste Embodiment

Various compositions of Exemplary Composition I were formulated and tested below. Toothpaste compositions and ingredients thereof tested (Toothpaste A through H) are summarized in Table 1. Table 2 provides a summary of the percentage weight to total weight of each ingredient in Toothpastes A to H.

TABLE 1

Comparison Toothpaste Compositions Ingredients

| Ingredient | Toothpaste A | Toothpaste B | Toothpaste C | Toothpaste D | Toothpaste E | Toothpaste F | Toothpaste G | Toothpaste H |
|---|---|---|---|---|---|---|---|---|
| Chlorite Ion Source | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide |
| Buffering System or pH adjusting agent | $Na_3HPO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ |
| Humectant(s) | Glycerin + Sorbitol | Sorbitol | — | — | — | — | Sorbitol | — |
| Aliphatic anionic compound | — | — | Sodium Lauroyl Sarcosinate | Sodium Lauroyl Sarcosinate | Sodium Cocoyl Sarcosinate | Sodium Myristoyl Sarcosinate | Sodium Lauroyl Sarcosinate | — |
| Source of Fluoride | — | Sodium Fluoride | Sodium Fluoride | — | Sodium Fluoride | Sodium Fluoride | Sodium Fluoride | Sodium Fluoride |
| Thickening Agent | Cellulose Gum | Cellulose Gum | Cellulose Gum | Cellulose Gum | Cellulose Gum | Cellulose Gum | Cellulose Gum | Cellulose Gum |
| Coloring Agent (whitening) | Titanium Dioxide | Titanium Dioxide | Titanium Dioxide | Titanium Dioxide | Titanium Dioxide | Titanium Dioxide | Titanium Dioxide | Titanium Dioxide |
| Abrasive Agent | Hydrated Silica | Hydrated Silica | Hydrated Silica | Hydrated Silica | Hydrated Silica | Hydrated Silica | Hydrated Silica | Hydrated Silica |
| Flavoring Agents(s) | Peppermint oil + Spearmint oil + Menthol Crystals | Peppermint oil + Menthol Crystals | Peppermint oil + Menthol Crystals | Peppermint oil + Menthol Crystals | Peppermint oil + Menthol Crystals | Peppermint oil + Menthol Crystals | Peppermint oil + Menthol Crystals | Peppermint oil + Menthol Crystals |
| Sweetener | Sodium Saccharin | Sucralose | Sucralose | Sucralose | Sucralose | Sucralose | Sucralose | Sucralose |
| Water | Water | Water | Water | Water | Water | Water | Water | Water |

Note:
$Na_3HPO_4$: Trisodium phosphate.
$Na_2HPO_4$: Disodium hydrogen phosphate.
$NaH_2PO_4$: Sodium dihydrogen phosphate.

TABLE 2

Toothpaste Compositions

| Ingredient | Toothpaste A (% w/w) | Toothpaste B (% w/w) | Toothpaste C (% w/w) | Toothpaste D (% w/w) | Toothpaste E (% w/w) | Toothpaste F (% w/w) | Toothpaste G (% w/w) | Toothpaste H (% w/w) |
|---|---|---|---|---|---|---|---|---|
| Stabilized Chlorine Dioxide | 0.14 | 0.14 | 0.14 | 0.14 | 0.14 | 0.14 | 0.14 | 0.14 |
| Trisodium phosphate | 1.0 | — | — | — | — | — | — | — |
| Disodium hydrogen phosphate + Sodium dihydrogen phosphate | — | 1.6 | 2.4 | 2.4 | 2.4 | 2.4 | 2.4 | 2.4 |

TABLE 2-continued

Toothpaste Compositions

| Ingredient | Toothpaste A (% w/w) | Toothpaste B (% w/w) | Toothpaste C (% w/w) | Toothpaste D (% w/w) | Toothpaste E (% w/w) | Toothpaste F (% w/w) | Toothpaste G (% w/w) | Toothpaste H (% w/w) |
|---|---|---|---|---|---|---|---|---|
| Glycerin | 10.0 | — | — | — | — | — | — | — |
| Sorbitol | 31.2 | 15.0 | — | — | — | — | 15.0 | — |
| Sodium Lauroyl Sarcosinate | — | — | 2.5 | 2.5 | — | — | 2.5 | — |
| Sodium Cocoyl Sarcosinate | — | — | — | — | 2.5 | — | — | — |
| Sodium Myristoyl Sarcosinate | — | — | — | — | — | 2.5 | — | — |
| Sodium Fluoride | — | 0.24 | 0.24 | — | 0.24 | 0.24 | 0.24 | 0.24 |
| Cellulose Gum | 1.2 | 1.9 | 1.9 | 1.9 | 1.9 | 1.9 | 1.9 | 1.9 |
| Titanium Dioxide | 0.95 | 0.95 | 0.95 | 0.95 | 0.95 | 0.95 | 0.95 | 0.95 |
| Hydrated Silica | 26.0 | 26.0 | 26.0 | 26.0 | 26.0 | 26.0 | 26.0 | 26.0 |
| Peppermint oil + Menthol Crystals | 0.9 | 0.9 | 0.9 | 0.9 | 0.9 | 0.9 | 0.9 | 0.9 |
| Sucralose | — | 0.1 | 0.2 | 0.2 | 0.2 | 0.2 | 0.2 | 0.2 |
| Sodium saccharin | 0.27 | — | — | — | — | — | — | — |
| Water | 28.34 | 53.17 | 64.77 | 65.01 | 64.77 | 64.77 | 49.77 | 67.27 |

Example 2: Accelerated Stability Testing of Toothpastes a, B, C. And D

Exemplary Toothpaste A was prepared following the teachings of U.S. Pat. Nos. 5,200,171, 5,348,734, and 5,489,435. pH of the composition containing stabilized chlorine dioxide was adjusted using only one pH adjusting agent, which is a. phosphate salt, trisodium phosphate. Toothpaste A contained glycerol and sorbitol as humectants.

Exemplary Toothpaste B was prepared following the teachings of U.S. Patent Application Publication No. 2011/0318282. Toothpaste B contained sorbitol as humectant but did not contain glycerol.

Exemplary Toothpastes C, E, and F were prepared following the teaching as described herein and according to Exemplary Composition I, wherein the stabilized chlorine dioxide compositions were free of both glycerol and sorbitol and contained N-acyl sarcosinate, an aliphatic anionic compound, such as sodium lauroyl sarcosinate, sodium cocoyl sarcosinate, and sodium myristoyl sarcosinate, respectively.

Exemplary Toothpaste D was prepared following the teaching as described herein, that is, that it was identical to Toothpaste C except for the absence of any fluoride ion source.

Exemplary Toothpaste G was prepared following the teaching as described herein and according to Exemplary Composition I, wherein the single-phase composition is comprised of sorbitol and sodium lauroyl sarcosinate.

Toothpaste H was prepared following the teaching as described herein and according to Exemplary Composition I, wherein the stabilized chlorine dioxide composition was free of sorbitol and an aliphatic anionic compound.

Accelerated stability testing of Toothpaste A, Toothpaste B, Toothpaste C, and Toothpaste D were performed at 40±2° C. and 70-75% relative humidity ("RH"). The results are summarized in Table 3. Accelerated stability testing at 40° C.±2° C. and 75%±5% RH is a standard accelerated stability test conducted in the pharmaceutical and cosmetic industries (Guidance for Industry: Q1A(R2) Stability Testing of New Drug Substances and Products, FDA, Revision 3 Nov. 2003). U.S. Pat. No. 6,696,047 describes the testing of oral care compositions claimed to maintain stable amounts of the chlorite ion at 25° C. for one year or 40° C. for 3 months. The stability testing of the compositions of Exemplary Composition I adheres to accepted norms of the pharmaceutical industry.

TABLE 3

Comparison of stability of toothpaste compositions at 40° ± 1° C. and 70-75% RH

| Composition | Initial SCD* (%) | 1 Month SCD (%) | 1 Month Loss (%) | 2 Months SCD (%) | 2 Months Loss (%) | 3 Months SCD (%) | 3 Months Loss (%) | 6 months SCD (%) | 6 months Loss (%) |
|---|---|---|---|---|---|---|---|---|---|
| Toothpaste A (Teachings of U.S. Pat. Nos. 5,200,171; 5,348,734; and 5,489,435) | 0.077 | 0.019 | 75.3 | 0.005 | 93.5 | 0.0025 | 96.7 | NT[§] | NT |

TABLE 3-continued

Comparison of stability of toothpaste compositions at 40° ± 1° C. and 70-75% RH

| Composition | Initial SCD* (%) | 1 Month SCD (%) | 1 Month Loss (%) | 2 Months SCD (%) | 2 Months Loss (%) | 3 Months SCD (%) | 3 Months Loss (%) | 6 months SCD (%) | 6 months Loss (%) |
|---|---|---|---|---|---|---|---|---|---|
| Toothpaste B (U.S. 2011/0318282) | 0.114 | 0.097 | 14.9 | 0.072 | 36.8 | 0.049 | 57.0 | NT | NT |
| Toothpaste C (Exemplary Composition I) | 0.12 | 0.12 | 0.0 | 0.11 | 8.3 | 0.10 | 16.6 | 0.09 | 25.0 |
| Toothpaste D (Exemplary Composition I) | 0.12 | 0.11 | 8.3 | 0.11 | 8.3 | 0.10 | 16.6 | 0.08 | 33.3 |

*SCD: Stabilized source of chlorine dioxide
§NT: Not Tested. The stability study for Toothpastes A and B was discontinued after observing unacceptable loss of 96.7% and 57.0% in 3 months.

As Table 3 shows, Toothpaste C and Toothpaste D provide much greater shelf-life stability than Toothpaste A and Toothpaste B as taught by prior art. Only 16.6% loss of stabilized source of chlorine dioxide in 3 months was observed for Toothpaste C and Toothpaste D. In contrast, Toothpaste A and Toothpaste B exhibited 96.7% and 57.0% loss of stabilized source of chlorine dioxide, respectively, in 3 months. The 75.3% loss of stabilized source of chlorine dioxide from Toothpaste A in 1 month demonstrates that the shelf life stability of Toothpaste A is less than 4 months at room temperature. Similarly, 36.8% loss of stabilized source of chlorine dioxide from Toothpaste B in 2 months demonstrates that the shelf life of Toothpaste B is less than 8 months at room temperature. Thus, both Toothpaste A and Toothpaste B do not provide shelf life stability of stabilized source of chlorine dioxide for a reasonable period of time, as defined herein, that is desirable for an over-the-counter consumer product. Importantly, 25.0% and 33.3% loos of stabilized source of chlorine dioxide in Toothpaste C and Toothpaste D after six months at 40° C., respectively, indicating that Toothpaste C and Toothpaste D have a shelf life of at least 24 months (2 years) at room temperature.

Example 3. Accelerated Stability Testing of Toothpastes A-H

Without being limited by scientific theory, the stability demonstrated by Toothpaste C and Toothpaste D is believed to be attributed to the inclusion of an aliphatic anionic compound in the single-phase composition, such as sodium lauroyl sarcosinate. The achieved stability of the source of chlorine dioxide in Toothpaste C and Toothpaste D is an unexpected result based on the tendency of source of chlorine dioxide to decompose or react with other components. Of note, the toothpaste embodiments, as tested, demonstrated a stable shelf-life for a single-phase composition comprising an oxidative compound, an aliphatic anionic compound, a buffering system, and carriers of the composition. Toothpaste C and D were stable for a reasonable period of time, e.g., from the time of compounding to a normal time of usage for topical OTC oral care products. The discovery of the effect of sodium lauroyl sarcosinate in increasing the stability of stabilized source of chlorine dioxide in Toothpastes C and D of Exemplary Composition I compared to Toothpastes A and B of the prior art is an unexpected result.

Further experiments were performed to verify the stabilizing benefit of an N-acyl sarcosinate with an oxidative compound. Toothpaste compositions containing N-acyl sarcosinate compounds such as sodium lauroyl sarcosinate (Toothpaste C), sodium cocoyl sarcosinate (Toothpaste E), and sodium myristoyl sarcosinate (Toothpaste F), as discussed in Exemplary Composition I were prepared and tested for their stability. Additionally, toothpaste containing N-acyl sarcosinate and sorbitol (Toothpaste G) and that does not contain sorbitol as well as N-acyl sarcosinate (Toothpaste H) were prepared and tested for their stability. The results are summarized in Table 4.

TABLE 4

Comparison of stability of Toothpastes prepared with different N-acyl sarcosinate compounds at 40° ± 1° C. and 70-75% RH

| Composition | Humectant | N-Acyl Sarcosinate | Initial SCD* (%) | 2 Month SCD (%) | 2 Month Loss (%) | 3 Month SCD (%) | 3 Month Loss (%) |
|---|---|---|---|---|---|---|---|
| Toothpaste A | Sorbitol + Glycerin | None | 0.077 | 0.005 | 93.5 | 0.0025 | 96.7 |
| Toothpaste B | Sorbitol | None | 0.114 | 0.072 | 36.8 | 0.049 | 57.0 |
| Toothpaste C | None | Sodium lauroyl sarcosinate | 0.12 | 0.11 | 8.3 | 0.10 | 16.6 |
| Toothpaste E | None | Sodium cocoyl sarcosinate | 0.14 | 0.14 | 0 | 0.13 | 9.3 |
| Toothpaste F | None | Sodium myristoyl sarcosinate | 0.13 | 0.13 | 0 | 0.14 | 0 |

TABLE 4-continued

Comparison of stability of Toothpastes prepared with different N-acyl sarcosinate compounds at 40° ± 1° C. and 70-75% RH

| | | | Initial | 2 Month | | 3 Month | |
|---|---|---|---|---|---|---|---|
| Composition | Humectant | N-Acyl Sarcosinate | SCD* (%) | SCD (%) | Loss (%) | SCD (%) | Loss (%) |
| Toothpaste G | Sorbitol | Sodium lauroyl sarcosinate | 0.14 | 0.13 | 7.3 | 0.13 | 9.5 |
| Toothpaste H | None | None | 0.13 | 0.13 | 0 | 0.13 | 9.5 |

*SCD: Stabilized source of chlorine dioxide

Exemplary Toothpastes C, E and F containing sodium lauroyl sarcosinate, sodium cocoyl sarcosinate, sodium myristoyl sarcosinate exhibited 16.6%, 9.3% and 0% loss in the stabilized source of chlorine dioxide after 3 months at 40±1° C. and 70-75% RH, respectively. As discussed earlier, the stability for 3 months at 40±1° C. and 70-75% RH corresponds to 1 year of shelf life at room temperature. The loss of stabilized source of chlorine dioxide in 3 months at 40±1° C. and 70-75% RH for toothpastes A and B prepared following teachings of prior patents as herein stated was 96.7% and 57.0%, respectively. Measurement variability in estimation of chlorine dioxide by titration method is about 10%. Therefore, any loss>10% is considered as observed loss. The results demonstrate that N-acyl sarcosinate compounds significantly enhanced the stability of stabilized source of chlorine dioxide. Toothpaste G that contains both sorbitol and sodium lauroyl sarcosinate exhibited 9.5% loss in stabilized source of chlorine dioxide in 3 months at 40±1° C. and 70-75% RH. Similarly, Toothpaste H that is essentially free of sorbitol exhibited 9.5% loss in stabilized source of chlorine dioxide in 3 months at 40±1° C. and 70-75% RH. The results confirm earlier finding that polyhydroxy compounds such as sorbitol and glycerin react with chlorite salts thereby resulting in unstable compositions.

In addition to the stability of stabilized source of chlorine dioxide consumer goodness properties such as flavor, taste, and consistency of the toothpaste are important for preparing a marketable composition. Viscosity of the toothpaste preparations was determined using Spindle 1 at 30 rpm. The results are summarized in Table 5.

TABLE 5

Viscosity of toothpaste preparations

| Exemplary Composition | Viscosity (Spindle 1 at 30 rpm) |
|---|---|
| Toothpaste A | 1531 cp |
| Toothpaste B | 1538 cp |
| Toothpaste C | 1544 cp |
| Toothpaste E | 1625 cp |
| Toothpaste F | 1263 cp |
| Toothpaste G | 2306 cp |
| Toothpaste H | 713 cp |

The viscosity data in Table 5 demonstrate significant differences for Toothpastes A-H. Viscosity of Toothpaste H was significantly lower (713 cp) compared to other toothpaste preparations, particularly Toothpastes A through F (range 1263 cp-1625 cp). Further, Toothpaste H did not form a uniform ribbon of toothpaste and did not hold or rest very well on a toothbrush. Thus, Toothpaste H did not achieve the desired consumer goodness characteristics for a consumer product toothpaste. On the other hand, viscosity of Toothpaste G was significantly higher (2306 cp) compared to other toothpaste preparations, particularly Toothpastes A through F (range 1263 cp-1625 cp). Toothpaste G was found to be difficult to squeeze out from the tubes at its viscosity and did not form a uniform ribbon. Accordingly, this level of viscosity renders it unsuitable as consumer product toothpaste. Thus, Toothpastes C, D, E and F comprise the stability, shelf-life and viscosity characteristics of a desired toothpaste embodiment.

Example 4: Enamel Fluoride Uptake and Remineralization and Demineralization

The following study was performed to determine the efficacy of an embodiment to (a) promote enamel fluoride uptake and (b) promote lesion remineralization under dynamic conditions simulating in vivo caries formation. The model and methods used are described in the literature (White 1987, 1988; Schemehorn et. al. 1990, 1992, 1994).

Test Products: US Pharmacopoeia Reference Standard for fluoride toothpaste i.e. Fluoride Dentifrice: Sodium Fluoride/Silica, Catalog No. 127752 was procured from US Pharmacopoeia store, 12601 Twinbrook Parkway, Rockville, Md. 20852-1790. Crest 3D White Mild Mint and Colgate Total Advanced Whitening Toothpaste were purchased from a local store. These commercially available toothpastes were selected because they were both comprised of sodium fluoride as a fluoride source, and thus were comparable to the Exemplary Toothpaste in this regard. Toothpaste B was prepared following the teachings of U.S. Patent Application Publication No. 2011/0318282. Exemplary Toothpaste C was prepared following the teaching as described herein and according to Exemplary Composition I.

Specimen Preparation: Enamel specimens (3 mm diameter) were removed from extracted bovine teeth and mounted in rods. The specimens were ground and polished to a high luster with Gamma Alumina using standard methods. Eighteen specimens per group were prepared for this study.

Initial Decalcification: Artificial lesions were formed in the enamel specimens by a 33-hour immersion into a solution of 0.1 M lactic acid and 0.2% Carbopol C907 which was 50% saturated with hydroxyapatite and adjusted to pH 5.0. The lesion surface hardness range was 25-45 Vickers microhardness (VHN; 200 gF, 15s dwell time) and average lesion depth was approximately 70 μm.

Remineralizing Solution: Pooled Human Saliva (collected fresh from multiple donors, pooled and kept frozen until time of use) was used as the remineralizing solution. Fifteen (15) ml of remineralizing solution was placed into color codes 30 ml treatment beakers. Fresh saliva was used each day (changed during the acid challenge period).

Treatment Slurries: During the treatment period, the specimens were immersed in dentifrice slurries to simulate daily brushing. The slurries were prepared by adding 5.0 g of Toothpaste B or Toothpaste C to 10 g of deionized water in a beaker with a magnetic stirrer. Fresh slurries were prepared for each of the two carriers just prior to each treatment.

Treatment Regimen: The cyclic treatment regimen consisted of a 4.0 hour/day acid challenge in the lesion forming solution described above with four, one-minute dentifrice treatment periods. After the treatments, the specimens were rinsed with running distilled water and then replaced back into the human saliva. The remaining time (~20 hours) the specimens were in the human saliva. The regimen was repeated for 10 days and interim Surface Micro-Hardness (SMH) measurements were obtained. The specimens were then subject to an additional 10 days of the treatment regimen for a total of 20 days. The treatment schedule used for this experiment was as follows (on the first day, Step 1 was not given; the test began with one hour in human saliva to permit pellicle development prior to any treatments):

| Step 1:- | 8:00 a.m.-8:01 a.m. | Dentifrice treatment |
| Step 2:- | 8:01 a.m.-9:00 a.m. | Remineralizing treatment |
| Step 3:- | 9:00 a.m.-9:01 a.m. | Dentifrice treatment |
| Step 4:- | 9:01 a.m.-10:00 a.m. | Remineralizing treatment |
| Step 5:- | 10:00 a.m.-2:00 p.m. | Acid challenge |
| Step 6:- | 2:00 p.m.-3:00 p.m. | Remineralizing treatment |
| Step 7:- | 3:00 p.m.-3:01 p.m. | Dentifrice treatment |
| Step 8:- | 3:01 p.m.-4:00 p.m. | Remineralizing treatment |
| Step 9:- | 4:00 p.m.-4:01 p.m. | Dentifrice treatment |
| Step 10:- | 4:01 p.m.-8:00 a.m. | Remineralizing treatment |
| Step 11:- | Back to Step 1 | |

Fluoride Analysis: At the end of the 20-day treatment regimen, the fluoride content of each enamel specimen was determined using the micro-drill technique to a depth of 100 µm. Fluoride data were calculated as µg F/cm$^3$ F×dilution factor/volume of drilling).

Remineralization Measurements: Both 10-day and 20-day Surface Micro Hardness (SMH) assessments were conducted. The difference between the hardness following treatment and initial lesion hardness indicated the ability of that treatment to enhance remineralization.

Figure 2:
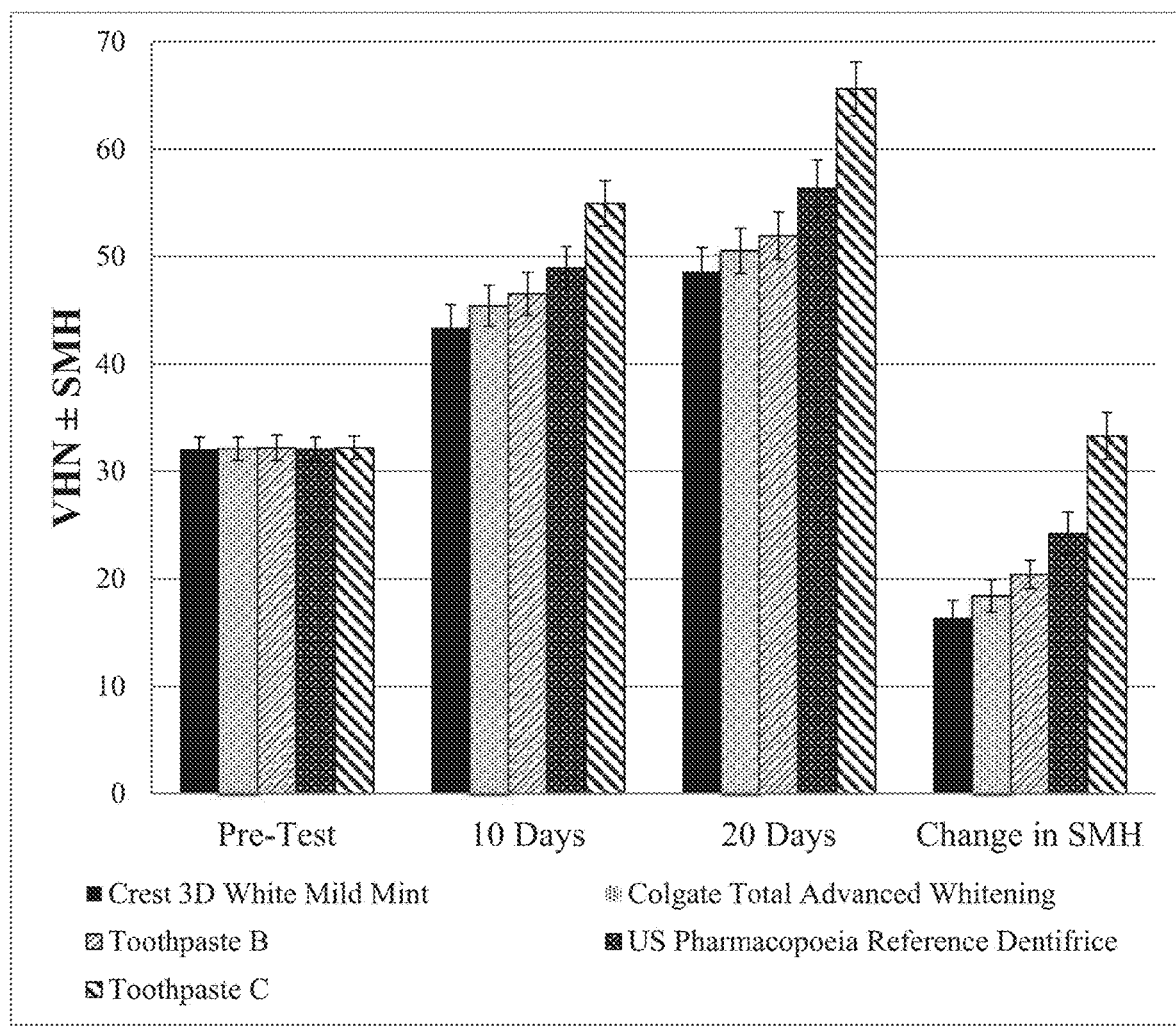
FIG. 2 is a graph illustrating tooth remineralization of commercial products to an oral care composition according to an embodiment.

Results: The fluoride uptake data is summarized in Table 6 and FIG. 1 and the summary of surface hardness changes representing remineralization is presented in Table 7 and FIG. 2. Statistical analyses were performed with a one-way analysis of variance model using Sigma Plot Software (13.0). Since significant differences were indicated, the individual means were analyzed by the Student Newman Keuls (SNK) test. All dentifrices tested contained the same amount of sodium fluoride (0.24% w/w), suggesting the observed differences in the enamel fluoride uptake remineralization were attributable to the combined effects of the components of Exemplary Composition I.

TABLE 6

Incipient Lesion Fluoride Uptake

| Toothpaste | Sodium Fluoride | Fluoride Uptake (µg F/cm$^3$) Mean (n = 18) | SEM |
|---|---|---|---|
| Crest 3D White Mild Mint | 0.243% | 1389 | ±64 |
| Colgate Total Advanced Whitening | 0.24% | 2697 | ±174 |
| U.S. Pharmacopoeia Reference Dentifrice | 0.24% | 2857 | ±187 |
| Toothpaste B | 0.24% | 3451 | ±202 |
| Toothpaste C | 0.24% | 5603 | ±365 |

Toothpaste C exhibited 62.3% more fluoride uptake into incipient lesioned enamel compared to Toothpaste B of U.S. Patent Application Publication No. 2011/0318282 (Table 6). Also, the fluoride uptake by Toothpaste C was 96.1%, 107.7%, and 303.3% higher than US Pharmacopoeia Reference Dentifrice, Colgate Total Advanced Whitening, and Crest 3D White Mild Mint toothpastes, respectively (Table 6). All tested toothpastes contained about 0.24% of sodium fluoride. However, Toothpaste C exhibited highest uptake of fluoride on tooth enamel. Combined effect of sodium lauroyl sarcosinate and stabilized source of chlorine dioxide in enhancing fluoride uptake in tooth enamel by Toothpaste C compared to Toothpaste B of prior art, US Pharmacopoeia Reference Material, and commercial products is an unexpected result.

TABLE 7

Surface Micro Hardness after 10 and 20 days of remineralization treatment

| | | Surface Micro Hardness (SMH) | | | | |
|---|---|---|---|---|---|---|
| | | Baseline | After 10 Days | | After 20 Days | |
| Toothpaste | Sodium Fluoride | (Pre-Test) SMH | SMH | Change in SMH | SMH | Change in SMH |
| Crest 3D White Mild Mint | 0.243% | 32.1 | 43.4 | 11.3 | 48.6 | 16.4 |
| Colgate Total Advanced Whitening | 0.24% | 32.1 | 45.4 | 13.3 | 50.5 | 18.4 |
| Toothpaste B | 0.24% | 32.2 | 46.5 | 15.0 | 51.9 | 20.4 |
| U.S. Pharmacopoeia Reference Dentifrice | 0.24% | 32.1 | 48.9 | 16.8 | 56.3 | 24.2 |
| Toothpaste C | 0.24% | 32.2 | 54.9 | 22.6 | 65.6 | 33.3 |

The protocol for the remineralization study involved repeated acid challenge and remineralization treatment. Therefore, net increased in Surface Micro-Hardness is the calculated combined result of enhanced remineralization and reduced demineralization. All toothpastes contained similar amounts of sodium fluoride (0.24% w/w). Nevertheless, Toothpaste C exhibited 63.2% more remineralization after 20 days compared to Toothpaste B of U.S. Patent Application Publication No. 2011/0318282 (Table 7). Also, the remineralization after 20 days by Toothpaste C was 37.6%, 80.9%, and 103.0% higher than US Pharmacopoeia Reference Dentifrice, Colgate Total Advanced Whitening, and Crest 3D White Mild Mint toothpastes, respectively. The remineralization results at 10 days and 20 days intervals were consistent further confirming increased remineralization (Table 7). All tested toothpastes contained about 0.24% of sodium fluoride. However, Toothpaste C exhibited highest tooth remineralization. An unexpected discovery from this study is the combined effect of sodium lauroyl sarcosinate and stabilized source of chlorine dioxide in a single-phase composition significantly increased remineralization (combined result of enhanced remineralization and reduced demineralization) over all other sodium fluoride-containing toothpastes tested.

Example 5: Pellicle Cleaning and Plaque Removal Study

The study below was performed to determine the plaque removal capability of an embodiment as determined by removal of stained pellicle. The method used was developed in order to assess the comparative ability of various dentifrices to remove stained pellicle, that is, to determine the cleaning ability of complete dentifrice formulations. Published studies demonstrate that the results of this test method with dentifrice slurries were comparable to those obtained in controlled clinical trials (Stookey et al. 1982). Thus, this methodology is known to those skilled in the art and is routinely used in the development of more effective cleaning dentifrice formulations.

Test Product: Toothpaste B was prepared following the teachings of U.S. Patent Application Publication No. 2011/0318282. Toothpaste C was prepared following the teaching as described herein. The American Dental Association (ADA) reference material was procured from Odontex Inc., Lawrence, Kans., USA.

Specimen Preparation: Bovine, permanent, central incisors were cut to obtain labial enamel specimens approximately 10×10 mm. The enamel specimens were embedded in an auto-polymerizing methacrylate resin so that only the enamel surfaces were exposed. The enamel surfaces were then smoothed and polished on a lapidary wheel and lightly etched to expedite stain accumulation and adherence. They were placed on a rotating rod (~37° C. incubator), which alternately exposed them to air and to a solution having PGY broth, tea, coffee, mucin, $FeCl_3$, and *Micrococcus luteus*. The staining broth was changed and specimens were rinsed daily until a uniform stain had accumulated. After approximately seven days, a darkly stained pellicle film was observed on the enamel surfaces. Specimens were rinsed, allowed to air dry, and refrigerated until used. All products were tested using specimens prepared at the same time.

Scoring and Set-Up: The amount of in vitro stain was graded photometrically using only the L value of the L*a*b* scale using a spectrophotometer (Minolta CM2600d). The area of the specimens scored was a ¼-inch diameter circle in the center of the 10×10 mm enamel. Specimens with scores between 30 and 42 (30 being more darkly stained) were used. On the basis of these scores, the specimens were divided into groups with each group having approximately the same average baseline score.

Procedure: The specimens were mounted on a mechanical V-8 cross-brushing machine equipped with soft nylon-filament (Oral-B 40) toothbrushes. Tension on the enamel surface was adjusted to 150 g. The dentifrices were tested as slurries prepared by mixing 25 grams of dentifrice with 40 ml of deionized water. The American Dental Association (ADA) Reference Material set the ADA abrasion standard (10 g/50 ml of a 0.5% CMC solution). The specimens were brushed for 800 strokes (4.5 minutes). To minimize mechanical variables, ten specimens per group were brushed on each of the eight brushing heads. Different test products were used on each run, with one tube of slurry made up for each product. Fresh slurry was made after being used to brush four specimens. Following brushing, specimens were rinsed, blotted dry, and scored again for stain, as previously described.

Calculations: The difference between the pre- and post-brushing stain scores was determined and the mean and standard error of measurement (SEM) was calculated for the reference group in each study. The mean decrement between the pre- and post-brushing stain scores was determined for the ADA Reference Material group, and assigned a pellicle cleaning ratio (PCR) value of 100. A constant value was calculated by dividing the mean decrement of the ADA Reference Material into 100. The individual PCR value for each specimen was calculated by multiplying its individual decrement by the calculated constant.

The mean, standard deviation and SEM for each test group were then calculated using the individual PCR values. The larger the PCR value, the greater the amount of stained pellicle removed from the enamel surface in this test. Data exhibiting outlier values was not considered for calculating pellicle cleaning ratio. The mean and SEM for each group was then calculated using the individual cleaning ratios. Data was analyzed using a one-way analysis of variance model (IBM SPSS Statistics 24 Software). Data was further analyzed doing all pairwise multiple comparison procedures (Student-Newman-Keuls method). All analyses were done with the significance level set at 0.05.

Results: Initially, the studies were conducted with 15 replicates (n=15) of each sample.

The mean pellicle cleaning ratio of Toothpaste B, Toothpaste C, and the ADA Reference Material were 95.9, 101.21, and 100.0, respectively. Further, the SEM around the mean was +2.46, +2.83, and +2.85, respectively. Therefore, exemplary Toothpaste C was significantly most effective in removing removal of stained pellicle than the ADA reference material and Toothpaste B. It is important to note that Toothpaste C exhibited 5.5% higher mean pellicle cleaning ratio on numerical basis compared to Toothpaste B. However, the difference was not statistically significant since the p value for the difference between the SEM around the mean for groups was >0.05. Because the testing was conducted with the routine number of replicates, the novel discovery of the current invention was not disclosed through this routine testing protocol.

The inventors repeated studies using 80 replicates (n=80) to provide a sufficiently robust number of replicates to account for the variability associated with the standard error of measurement (SEM) and allow the outcomes of the discovery to be revealed as statistically significant. The results are summarized in the Table 8.

TABLE 8

Pellicle Cleaning Ratio of Dentifrices

| Toothpaste | n | Pellicle Cleaning Ratio Mean | SEM |
|---|---|---|---|
| Toothpaste B | 76 | 94.48 | ±1.12 |
| ADA Reference Material | 75 | 100.00 | ±1.20 |
| Toothpaste C | 75 | 103.51 | ±0.96 |

The observation that Exemplary Toothpaste C was significantly more effective in removal of stained pellicle than the ADA reference material and Toothpaste B as affirmed with the higher number of replicates. Further, Toothpaste B was less effective in removal of stained pellicle compared to ADA reference material. Importantly, the p-value for the difference between the groups was <0.05. Therefore, removal of stained pellicle Toothpaste C compared to Toothpaste B of U.S. Patent Application Publication No. 2011/0318282 and the ADA Reference Material was statistically significant. Combined effect of sodium lauroyl sarcosinate and stabilized source of chlorine dioxide in enhancing removal of stained pellicle that corresponds to plaque removal from tooth enamel by Toothpaste C compared to Toothpaste B of prior art and ADA Reference Material is an unexpected result. The results demonstrate that the results of Toothpaste C were unexpected over the prior art.

Example 6: Regrowth of Oral Polymicrobial Biofilm

The following study was performed to determine the effect of an embodiment on preventing 24 hours regrowth of oral polymicrobial biofilm containing a mixed salivary bacterial preparation on bovine enamel surfaces.

Test Product: Exemplary Toothpaste C was prepared following the teaching as described herein.

Experimental Design: 4×4 mm bovine enamel sections (embedded in 12×12×7 mm acrylic resin) were prepared for use in sterile 12 well tissue culture plates and sterilized by ethylene oxide (EtO). Three ml of Brain Heart Infusion broth supplemented with Yeast Extract and Vitamin K and hemin (BHI-YE) was inoculated with 50 µl of an overnight culture of a mixed species whole salivary bacterial preparation in the wells of the tissue culture plate containing the sections (1 section/well). The plates were incubated for 24 hours to grow the biofilm on the enamel. In order to remove the biofilm similar to a human subject brushing his/her teeth, the sections were brushed with Toothpaste C (3 sections/paste) for a brushing schedule similar to a 30 second brushing by human subjects. The sections were rinsed with sterile water and inserted into a fresh tissue culture plate containing 3 ml of BHI-YE to facilitate regrowth of the remaining oral biofilm on the enamel sections. The plates were incubated for 24 hours. The sections were removed, placed in 2 ml of sterile saline, sonicated for 10 sec, vortexed for 10 sec, diluted to 1:10 and 1:1000 and spiral plated on blood agar plates. After 24 hours of incubation, the colonies on the agar plates were counted using an automated colony counter. The methods used are described in published literature (Huang et al. 2012 and Sabrah et al. 2015).

Results: The results of the biofilm viability (CFU/ml) assay are presented in Table 9.

TABLE 9

Regrowth of Oral Polymicrobial Biofilm

| Sample number | Mean CFU/ml | Group Mean CFU/ml | p value compared to Control |
|---|---|---|---|
| Toothpaste C-1 | $1.04 \times 10^7$ | $5.08 \times 10^7$ | 0.018 |
| Toothpaste C-2 | $1.39 \times 10^8$ | | |
| Toothpaste C-3 | $3.18 \times 10^6$ | | |
| Control-1 | $8.31 \times 10^7$ | $13.1 \times 10^7$ | NA |
| Control-2 | $9.96 \times 10^7$ | | |
| Control-3 | $2.09 \times 10^8$ | | |

Exemplary toothpaste C was discovered to provide a significant reduction in regrowth of oral polymicrobial biofilm when compared to the water brushed control (p<0.05). Regrowth of oral polymicrobial biofilm is directly proportional to quantity of residual bacteria after brushing. Therefore, the results demonstrate the Toothpaste C is significantly and highly effective killing bacteria in oral polymicrobial biofilm.

Example 7: Spectrometric Analysis of Various Embodiments

The following study was performed to determine the quantity of chlorite ion available in an embodiment of the present disclosure. Such available quantity of chlorite ion and not the stabilized source of chlorine dioxide is important for reaction with the salivary biomolecules in the oral cavity. The methodology used was standard UV-visible spectrometry.

Test Products: Toothpaste B was prepared following the teachings of U.S. Patent Application Publication No. 2011/0318282. Exemplary Toothpaste C was prepared following the teaching as described herein. Sodium chlorite was purchased from Sigma-Aldrich, 3050 Spruce St., St. Louis, Mo. 63103.

Specimen Preparation: 0.02 mM phosphate buffer pH 7.0 was prepared using HPLC grade water. 200 mg of toothpaste A and toothpaste B were suspended in 3.0 ml of 0.02 mM phosphate buffer pH 7.0 and homogenized thoroughly using rotamix. The homogenous mixtures were then centrifuged at 3,500 rpm for 30 minutes. Clear supernatants were collected. Aqueous toothpaste extracts were used for spectrophotometric analysis. Each toothpaste product was processed in 5 replicates. pH adjusted HPLC-grade water served as a suitable control for recording the spectra.

Recording of Spectra: Zero-order electronic absorption spectra of aqueous extracts of toothpaste products and aqueous authentic sodium chlorite ($Na^+/ClO_2^-$) solution were recorded on a PC-controlled Jasco V730 UV-visible spectrophotometer at a pH value of 7.0 (scan rate 120 nm/min). From the extinction coefficient ($\varepsilon$) values of $ClO_2^-$ and $OCl^-$ (at max values of 262 and 292 nm, respectively), multivariate spectral curve resolution analysis of datasets consisting of a range of oral dilutions were subjected to multivariate curve resolution (MCR) analysis for determining the concentration of chlorite ion ($ClO_2^-$; predominant active agent).

Figure 3:
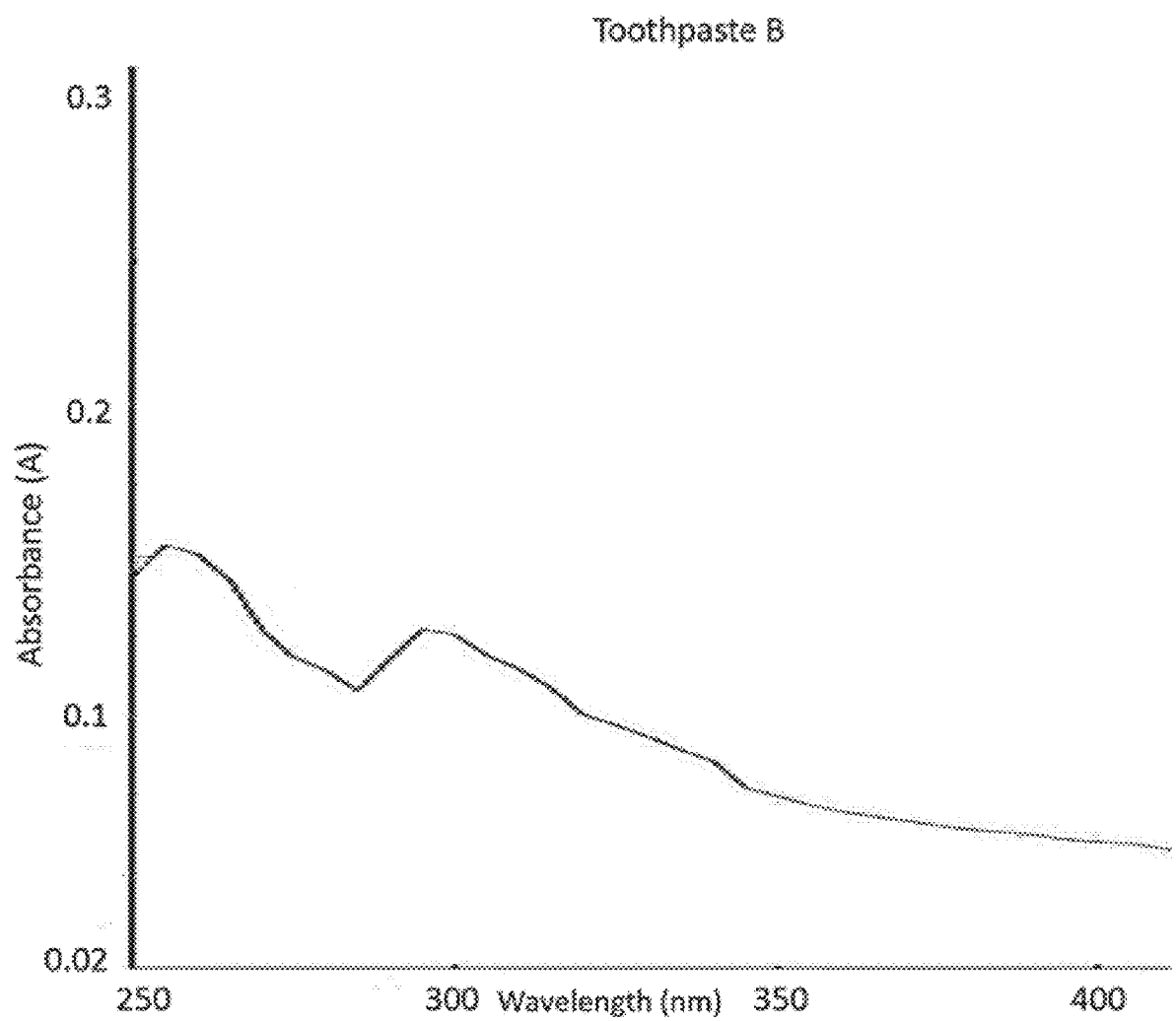
FIG. 3 illustrates zero-order electronic absorption spectra of aqueous extracts of Toothpaste B.
Figure 4:
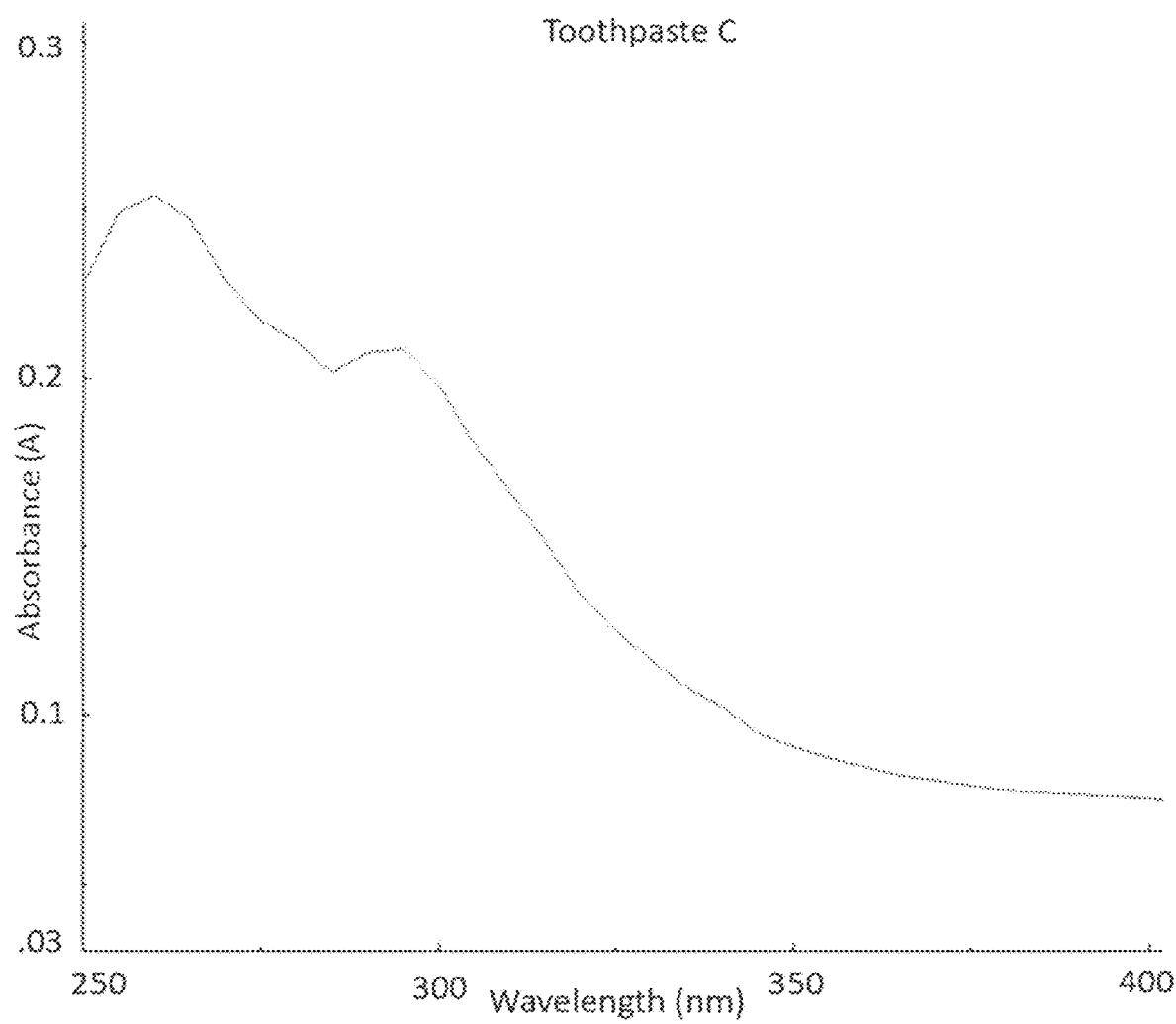
FIG. 4 illustrates zero-order electronic absorption spectra of aqueous extracts of Toothpaste C.

Results: Electronic absorption spectra of Toothpaste B and Toothpaste C are presented in FIG. 3 and FIG. 4, respectively.

Both Toothpaste B and Exemplary Toothpaste C showed two clear absorption bands located at 262 nm and 295 nm. Absorption peak at 262 nm corresponds to active chlorite anion and the peak at 295 nm is attributed to hypochlorite anion generated from the decomposition of chlorite, and/or chemical reaction of chlorite with other ingredient in the toothpaste. Absorbance peak of chlorite ion (ClO2) at 262 nm of Toothpaste B was 0.155 and that for Toothpaste C was 0.255. The higher absorbance in Toothpaste C provides evidence of a 64.5% higher quantity of available chlorite ion ($ClO_2^-$) compared to Toothpaste B. The significantly higher amount of available chlorite ion yielded by Toothpaste C compared to Toothpaste B was unexpected. Not to be bound by any particular theory, a benefit of having 64.5% more available chlorite ion is its bioavailability and potential for greater efficacy for antimicrobial uses in the oral cavity. This finding of greater bioavailability of the chlorite ion in the Exemplary Toothpaste C is further provided and confirm the testing of oxidation of salivary biomolecules such as pyruvate and L-methionine as described in Example 8.

Example 8: Oxidation of Salivary Biomolecules by $^1$H NMR Analysis

The following study was performed to determine the efficacy of an embodiment of the present disclosure for oxidation of biomolecules in saliva. Oxidation of pyruvate to acetate and L-methionine to methionine sulfoxide was monitored by $^1$H NMR spectroscopy.

Test Products: Toothpaste B was prepared following the teachings of U.S. Patent Application Publication No. 2011/0318282. Exemplary Toothpaste C was prepared following the teaching as described herein.

Aqueous Toothpaste Extract Preparation: 0.02 mM phosphate buffer pH 7.0 was prepared using HPLC grade water. 200 mg of Toothpaste B and Exemplary Toothpaste C was suspended in 3.0 ml of 0.02 mM phosphate buffer pH 7.0 and homogenized thoroughly using rotamix. The homogenous mixture was then centrifuged at 3,500 rpm for 30 minutes. Clear supernatant was collected. Aqueous toothpaste extracts thus prepared was used for the study.

Human Saliva Sample Preparation: 0.6 ml of aqueous extract of the toothpaste composition to be tested was mixed with 0.6 ml of aliquots of each salivary supernatant sample collected from healthy volunteers (n=10). After thorough rotamixing, these mixtures were equilibrated at a temperature of 35° C. for 30 and 60 second periods, and then stored at −80° C. for a maximal duration of 72 hours prior to $^1$H NMR analysis. 0.6 ml aliquots of each salivary supernatant sample mixed with 0.6 ml of HPLC-grade water (previously thoroughly sparged with Helium gas for a 30 min. period) in place of the extracts of toothpaste products and then also equilibrated and stored in the same manner served as essential controls.

Time Dependent Oxidation of Pyruvate to Acetate and Methionine to Methionine Sulfoxide: Aqueous solutions containing 0.02 mM of sodium pyruvate and L-methionine were prepared in 0.05 mM phosphate buffer (pH 7.0) and rigorously deoxygenated via purging with Helium gas for 30 mins at ambient temperature prior to use. 1.00 ml aliquots of this solution were individually treated with equivalent volumes of aqueous extract of the toothpaste composition. The mixture was then equilibrated at a temperature of 35° C. for 30 and 60 seconds and stored at −80° C. for a maximal period of 72 hours prior to the acquisition of $^1$H NMR spectra. 1.0 ml aliquots of sodium pyruvate or L-methionine solution treated with an equivalent volume of HPLC-grade water equilibrated and stored in the same manner served as respective control.

$^1$H NMR Measurements: A 0.60 ml aliquot of sample prepared as described above was placed in 5-mm diameter NMR tubes and 0.1 ml of a 0.00225 mM solution of sodium 3-trimethylsilyl-(2,2,3,3-2H4)-1-propionate [TSP, internal chemical shift reference and quantitative $^1$H NMR internal standard (δ=0.00 ppm)] in deuterium oxide ($^2H_2O$) was added, the latter to provide a field frequency lock. Single-pulse and/or Carr-Purcell-Meiboom-Gill (CPMG) spin-echo $^1$H NMR spectra was acquired on a Bruker Avance AV-400 spectrometer at an operating frequency of 399.94 MHz and a probe temperature of 293 K. The one-dimensional (1D) NOESY pulse sequence with presaturation of the biofluid water signal were employed throughout. Chemical shift values were referenced to the added TSP for these samples, together with the —$CH_3$ group signals of selected biomolecules detectable. All $^1$H NMR spectra were acquired in duplicate, a random order and an automated manner using a sample changer for continuous sample delivery. Two-dimensional (2D) shift-correlated $^1$H-$^1$H spectra of biofluid samples were also acquired.

Results: $^1$H NMR-linked metabolomics analysis of human salivary sample supernatants revealed that aqueous extract from Exemplary Toothpaste C formulation was significantly more effective than those from Toothpaste B in oxidation of pyruvate to acetate and methionine to methionine sulfoxide. Repeated testing confirmed this conclusion. The finding was further confirmed by a time dependent study wherein solutions of sodium pyruvate and methionine were treated with aqueous extracts of Toothpaste B and Exemplary Toothpaste C each for 30 and 60 seconds. The results are summarized in Table 10.

TABLE 10

Oxidation of Salivary Biomolecules as Determined by $^1$H NMR Study

| | Oxidation of Sodium Pyruvate [Acetate]:[Pyruvate] Ratio | | Oxidation of L-Methionine [Methionine Sulfoxide]:[Methionine] | |
|---|---|---|---|---|
| Time | Toothpaste B | Toothpaste C | Toothpaste B | Toothpaste C |
| 0 Seconds | $0.149 \times 10^{-3}$ | $0.149 \times 10^{-3}$ | $1.58 \times 10^{-3}$ | $1.69 \times 10^{-3}$ |
| 30 Seconds | $1.30 \times 10^{-3}$ | $9.57 \times 10^{-3}$ | $5.55 \times 10^{-3}$ | $13.0 \times 10^{-3}$ |
| 60 Seconds | $3.08 \times 10^{-3}$ | $11.30 \times 10^{-3}$ | $5.75 \times 10^{-3}$ | $14.0 \times 10^{-3}$ |

The ratio of concentrations of acetate:pyruvate within 30 and 60 seconds of interaction with Exemplary Toothpaste C was 7.36 and 3.66 times higher than Toothpaste B, respectively. Similarly, the ratio of concentrations of methionine sulfoxide:methionine within 30 and 60 seconds of interaction with Toothpaste C was 2.34 and 2.43 times higher than Toothpaste B, respectively. The results confirmed the unanticipated discovery that Toothpaste C oxidized salivary biomolecules at significantly faster rate and in significantly greater quantity than Toothpaste B.

The relatively lower oxidizing activity of Toothpaste B in this study is attributed to the partial consumption of stabilized source of chlorine dioxide by sorbitol present in the formula, reducing the bioavailability of the chlorite ion. Sorbitol is known in the art to react with chlorine dioxide. The results are also aligned with the lower stability of stabilized source of chlorine dioxide of Toothpaste B (as presented in Table 3). Combined effect of sodium lauroyl sarcosinate and stabilized source of chlorine dioxide in enhancing the oxidation of salivary biomolecules by Toothpaste C over Toothpaste B is an unexpected result. The results demonstrate that Toothpaste C was more effective at oxidizing sodium pyruvate and L-methionine over the prior art. Not to be bound by a particular theory, the increased levels of sodium chlorite seen in Example 7 may have led to the increased oxidation reaction. Though this may be true, this is not the only factor that may contribute to the heightened oxidative reaction. Physio-chemical properties of other components in the embodiments may also contribute. The altered microenvironment of hydrophilicity due to an N-acyl sarcosinate may also contribute to higher oxidation reaction.

Example 9: Additional Formulations of Toothpaste Embodiments

Toothpaste compositions and ingredients thereof tested (Toothpaste B and Exemplary Toothpastes C, and I through M) are summarized in Table 11. Table 12 provides a summary of the percentage weight to total weight of each ingredient in Toothpaste B and Exemplary Toothpastes C, and I through M.

TABLE 11

Comparison of Toothpaste Compositions Ingredients

| Ingredient | Toothpaste B | Toothpaste C | Toothpaste I | Toothpaste J | Toothpaste K | Toothpaste L | Toothpaste M |
|---|---|---|---|---|---|---|---|
| Chlorite Ion Source | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide |
| Buffering System or pH adjusting agent | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ |
| Humectant(s) | Sorbitol | — | — | — | — | — | — |
| Aliphatic anionic compound | — | Sodium Lauroyl Sarcosinate | Sodium Myristoyl Sarcosinate | Sodium Myristoyl Sarcosinate | Sodium Myristoyl Sarcosinate | Sodium Myristoyl Sarcosinate | Sodium Myristoyl Sarcosinate |
| Source of Fluoride | Sodium Fluoride | Sodium Fluoride | Sodium Fluoride | Sodium Fluoride | Sodium Fluoride | Sodium Fluoride | Sodium Fluoride |
| Thickening Agent | Cellulose Gum | Cellulose Gum | Cellulose Gum | Cellulose Gum | Cellulose Gum | Cellulose Gum | Cellulose Gum |
| Coloring Agent (whitening) | Titanium Dioxide | Titanium Dioxide | Titanium Dioxide | Titanium Dioxide | Titanium Dioxide | Titanium Dioxide | Titanium Dioxide |
| Abrasive Agent | Hydrated Silica | Hydrated Silica | Hydrated Silica | Hydrated Silica | Hydrated Silica | Hydrated Silica | Hydrated Silica |
| Flavoring Agents(s) | Peppermint oil + Menthol Crystals | Peppermint oil + Menthol Crystals | Peppermint oil + Menthol Crystals | Peppermint oil + Menthol Crystals | Peppermint oil + Menthol Crystals | Watermelon | Strawberry |
| Sweetener | Sucralose | Sucralose | Sucralose | Sucralose | Sucralose | Sucralose | Sucralose |
| Water | Water | Water | Water | Water | Water | Water | Water |

Note:
$Na_2HPO_4$: Disodium hydrogen phosphate.
$NaH_2PO_4$: Sodium dihydrogen phosphate.

TABLE 12

Toothpaste Compositions

| Ingredient | Toothpaste B (% w/w) | Toothpaste C (% w/w) | Toothpaste I (% w/w) | Toothpaste J (% w/w) | Toothpaste K (% w/w) | Toothpaste L (% w/w) | Toothpaste M (% w/w) |
|---|---|---|---|---|---|---|---|
| Stabilized Chlorine Dioxide | 0.14 | 0.14 | 0.14 | 0.14 | 0.14 | 0.14 | 0.14 |
| $Na_2HPO_4$ + $NaH_2PO_4$ | 1.6 | 2.4 | 2.4 | 2.4 | 2.4 | 2.4 | 2.4 |
| Sorbitol | 15.0 | — | — | — | — | — | — |
| Sodium Lauroyl Sarcosinate | — | 2.5 | — | — | — | — | — |
| Sodium Myristoyl Sarcosinate | — | — | 1.25 | 0.65 | 0.25 | 0.25 | 0.25 |
| Sodium Fluoride | 0.24 | 0.24 | 0.21 | 0.21 | 0.21 | 0.21 | 0.21 |
| Cellulose Gum | 1.9 | 1.9 | 1.9 | 1.9 | 1.9 | 1.9 | 1.9 |
| Titanium Dioxide | 0.95 | 0.95 | 0.95 | 0.95 | 0.95 | 0.95 | 0.95 |
| Hydrated Silica | 26.0 | 26.0 | 26.0 | 26.0 | 26.0 | 26.0 | 26.0 |

TABLE 12-continued

Toothpaste Compositions

| Ingredient | Toothpaste B (% w/w) | Toothpaste C (% w/w) | Toothpaste I (% w/w) | Toothpaste J (% w/w) | Toothpaste K (% w/w) | Toothpaste L (% w/w) | Toothpaste M (% w/w) |
|---|---|---|---|---|---|---|---|
| Peppermint oil + Menthol Crystals | 0.9 | 0.9 | 0.9 | 0.9 | 0.9 | — | — |
| Watermelon Flavor | — | — | — | — | — | 0.5 | — |
| Strawberry Flavor | — | — | — | — | — | — | 0.5 |
| Sucralose | 0.1 | 0.2 | 0.2 | 0.2 | 0.2 | 0.2 | 0.2 |
| Water | 53.17 | 64.77 | 66.05 | 66.65 | 67.05 | 67.45 | 67.45 |

Note:
$Na_2HPO_4$: Disodium hydrogen phosphate.
$NaH_2PO_4$: Sodium dihydrogen phosphate.

Toothpaste B was prepared following the teachings of U.S. Patent Application Publication No. 2011/0318282. Toothpaste B contained sorbitol as humectant but did not contain an aliphatic anionic compound.

Toothpastes C was prepared following the teachings of U.S. Patent Application Publication No. 2019/0070085 Toothpaste C was free of sorbitol and contained N-acyl sarcosinate, an aliphatic anionic compound, in the form of sodium lauroyl sarcosinate.

Exemplary Toothpastes I through M were prepared following the teaching as described herein and according to Exemplary Composition I, wherein the compositions were free of sorbitol and contained N-acyl sarcosinate, an aliphatic anionic compound, such as sodium myristoyl sarcosinate, as indicated in Table 12.

Composition of Toothpastes I through K were identical except for the quantity of sodium myristoyl sarcosinate.

Ingredients of Toothpastes L and M were identical to Toothpaste K except for flavoring system.

Example 10: Accelerated Stability Testing of B, C, K, L and M

Accelerated stability testing of Toothpaste B, Toothpaste C, Toothpaste K, Toothpaste L, and Toothpaste M, were performed at 40±1° C. and 70-75% relative humidity ("RH"). The results are summarized in Table 13. Accelerated stability testing at 40° C.±2° C. and 75%±5% RH is a standard accelerated stability test conducted in the pharmaceutical and cosmetic industries (Guidance for Industry: Q1A(R2) Stability Testing of New Drug Substances and Products, FDA, Revision 3 Nov. 2003). Oral care compositions claimed to maintain stable amounts of the chlorite ion at 25° C. for one year or 40° C. for 3 months is described in U.S. Pat. No. 6,696,047. The stability testing of the compositions of Exemplary Composition I adheres to accepted norms of the pharmaceutical industry.

TABLE 13

Comparison of stability of toothpaste compositions at 40° ± 1° C. and 70-75% RH

| Composition | Initial SCD* (%) | 1 Month SCD (%) | 1 Month Loss (%) | 2 Months SCD (%) | 2 Months Loss (%) | 3 Months SCD (%) | 3 Months Loss (%) | 6 months SCD (%) | 6 months Loss (%) |
|---|---|---|---|---|---|---|---|---|---|
| Toothpaste B (U.S. 2011/0318282) | 0.114 | 0.097 | 14.9 | 0.072 | 36.8 | 0.049 | 57.0 | NT[§] | NT |
| Toothpaste C (U.S. 2019/0070085) | 0.12 | 0.12 | 0.0 | 0.11 | 8.3 | 0.10 | 16.6 | 0.09 | 25.0 |
| Toothpaste K (Exemplary Composition I) | 0.13 | 0.13 | 0.0 | 0.12 | 7.7 | 0.11 | 15.4 | 0.09 | 30.8 |
| Toothpaste L (Exemplary Composition I) | 0.13 | 0.12 | 7.7 | 0.12 | 7.7 | 0.11 | 15.4 | NT | NT |
| Toothpaste M (Exemplary Composition I) | 0.12 | 0.11 | 8.3 | 0.10 | 16.7 | 0.12 | 0.0 | NT | NT |

*SCD: Stabilized chlorine dioxide
[§]NT: Not Tested.

As Table 13 shows, the composition of Toothpaste C (prepared as taught in U.S. Patent Application Publication No. 2019/0070085) provides significantly greater shelf-life stability than Toothpaste B (Toothpaste B was prepared following the teachings of U.S. Patent Application Publication No. 2011/0318282). Sorbitol (polyhydroxy alcohol) present in Toothpaste B is known to react and degrade sodium chlorite. Toothpastes K, L, and M contain N-acyl sarcosinate compound sodium myristoyl sarcosinate and are devoid of sorbitol; they exhibit stability comparable to Toothpaste C. Toothpastes C and K through M exhibited less than 17.0% loss of stabilized source of chlorine dioxide in 3 months while Toothpaste B showed 57.0% in 3 months and. 36.8% loss of stabilized source of chlorine dioxide in 2 months, thereby demonstrating that the shelf life of Toothpaste B is less than 8 months at room temperature. Thus, Toothpaste B, representing prior art, does not provide shelf life stability of stabilized source of chlorine dioxide for a reasonable period of time, as defined herein, that is desirable for an over-the-counter consumer product.

Toothpaste C and Toothpaste K exhibited 25.0% and 30.8% loss of stabilized source of chlorine dioxide, respectively, after six months at 40° C., indicating that Toothpaste C and Toothpaste K have a shelf life of at least 24 months (2 years) at room temperature. The compositions of Toothpastes L and M are identical to the composition of Toothpaste K except for the flavoring system. Also, the loss of stabilized source of chlorine dioxide at 1, 2, and 3-month time points for Toothpastes L and M is comparable to Toothpastes C and K. Therefore, Toothpastes L and M also would provide a shelf life of at least 24 months (2 years) at room temperature. Toothpaste M exhibited no loss in stabilized source of chlorine dioxide at 3 months when compared to losses of 8.3% and 16.7% in 1 and 2-month, respectively. Such variation in loss of stabilized chlorine dioxide in Toothpaste M may be due to (i) the concentration of stabilized source of chlorine dioxide being very low and the slight difference in value at second decimal digit significantly contributing to the percent calculation and (ii) persons skilled in the art understand that one analytical method for estimation of stabilized chlorine dioxide is based on titration and therefore may exhibit inherent variability. Therefore, interpretation of stability results is preferably based on the concentration of stabilized source of chlorine dioxide. Attention is drawn to the results in Table 13; at 3-month time point the concentration of stabilized chlorine dioxide in Toothpastes C through M was about 0.1% whereas that in Toothpaste B was about 0.05%

Example 11: Enamel Fluoride Uptake and Remineralization and Demineralization

The following study was performed to determine the efficacy of an embodiment of the Present Invention to (a) promote enamel fluoride uptake and (b) promote lesion remineralization under dynamic conditions simulating in vivo caries formation. The model and methods used are described in the literature (White 1987, 1988; Schemehorn et. al. 1990, 1992, 1994).

Test Products: US Pharmacopoeia Reference Standard for fluoride toothpaste i.e. Fluoride Dentifrice: Sodium Fluoride/Silica, Catalog No. 127752 was procured from US Pharmacopoeia store, 12601 Twinbrook Parkway, Rockville, Md. 20852-1790. Exemplary Toothpaste K was prepared following the teaching as described herein and according to Exemplary Composition I.

Experimental Protocol: The experimental protocols for fluoride uptake and remineralization were as described in Example 4 herein.

Fluoride Analysis: At the end of the 20-day treatment regimen, the fluoride content of each enamel specimen was determined using the micro-drill technique to a depth of 100 µm. Fluoride data were calculated as µg F/cm3 (µg F×dilution factor/volume of drilling).

Remineralization Measurements: Surface Micro Hardness (SMH) assessments were conducted at the end of the $20^{th}$ day. The difference between the hardness following treatment and initial lesion hardness indicated the ability of that treatment to enhance remineralization.

Results: The fluoride uptake data is summarized in Table 14 and the summary of surface hardness changes representing remineralization is presented in Table 15. Statistical analyses were performed with a one-way analysis of variance model using Sigma Plot Software (13.0). Since significant differences were indicated, the individual means were analyzed by the Student Newman Keuls (SNK) test. Enamel fluoride uptake and relative change in surface micro hardness (ASMH) results for USP Reference Material were designated as 100% and values for individual toothpastes were normalized with USP Reference Material. In this manner, the normalization of the results of Toothpaste C to the USP Reference Material and the results of Toothpaste K to the USP Reference Material were performed independently. In that regard, it is noted that comparing the normalized mean fluoride uptake and remineralization of Toothpaste C to Toothpaste K is likely not informative.

TABLE 14

Incipient Lesion Fluoride Uptake after 20 days

| Toothpaste | Sodium Fluoride | Mean fluoride uptake (%) |
| --- | --- | --- |
| U.S. Pharmacopoeia Reference Dentifrice | 0.24% | 100 |
| Toothpaste C | 0.24% | 196.1 |
| Toothpaste K | 0.21% | 127.4 |

*The results were normalized with USP Reference Material.

The fluoride uptake by Toothpaste K was 27.4%, higher than US Pharmacopoeia Reference Dentifrice (Table 14). The concentration of sodium fluoride in Toothpaste K was lower than US Pharmacopoeia Reference Dentifrice (0.21% vs. 0.24%). However, Toothpaste K achieved higher fluoride uptake on tooth enamel. This is unexpected result. The higher fluoride uptake by Toothpaste K is attributed to combined effect of sodium fluoride, N-acyl sarcosinate and stabilized source of chlorine dioxide.

The results previously presented in Table 6 demonstrate that fluoride uptake by US Pharmacopoeia Reference Dentifrice was 5.9% and 105.6% higher than Colgate Total Advanced Whitening and Crest 3D White Mild Mint toothpastes, respectively. Since the same testing protocol and methods were applied in the testing of Exemplary Toothpaste K, one can conclude that the fluoride uptake by Toothpaste K was significantly higher than Colgate Total Advanced Whitening and Crest 3D White Mild Mint toothpastes.

TABLE 15

Surface Micro Hardness after 20 days of remineralization treatment

| Toothpaste | Sodium Fluoride | Relative Change in SMH after 20 days* |
|---|---|---|
| U.S. Pharmacopoeia Reference Dentifrice | 0.24% | 100% |
| Toothpaste C | 0.24% | 136.7% |
| Toothpaste K | 0.21% | 177.8% |

*The results were normalized with USP Reference Material.

The protocol for the remineralization study involved repeated acid challenge and remineralization treatment. Therefore, net increased in Surface Micro-Hardness is combined result of enhanced remineralization and reduced demineralization.

The Surface Micro-Hardness after 20 days by Toothpaste K was 77.8% higher than US Pharmacopoeia Reference Dentifrice (Table 15). The concentration of sodium fluoride in Exemplary Toothpaste K was lower than US Pharmacopoeia Reference Dentifrice (0.21% vs. 0.24%). However, Toothpaste K achieved higher remineralization of tooth enamel. This is an unexpected discovery. The higher remineralization by Toothpaste K is attributed to combined effect of sodium fluoride, N-acyl sarcosinate and stabilized source of chlorine dioxide.

The results presented in Table 7 demonstrate that remineralization after 20 days by US Pharmacopoeia Reference Dentifrice was 31.5% and 47.5% higher than Colgate Total Advanced Whitening and Crest 3D White Mild Mint toothpastes, respectively. As the same testing method was applied to Toothpaste K, it can be concluded that remineralization by Toothpaste K was significantly higher than Colgate Total Advanced Whitening and Crest 3D White Mild Mint toothpastes, It is anticipated that Exemplary Toothpastes L and M would give similar higher results for enamel fluoride uptake and Surface Micro Hardness since the compositions of Toothpastes L, and M are identical to Toothpaste K except for the flavor system.

Fluoride uptake method measures fluoride uptake within the tooth, that is, both on surface and deep inside. Change in Surface Micro Hardness may be seen as a measure of remineralization on the surface. Importantly, remineralization is a complex phenomenon and availability of fluoride (or fluoride uptake) at the remineralization site is a first step. Therefore, it is evident that fluoride uptake by Toothpaste K is greater at the surface where the remineralization process takes place. Fluoride uptake by Toothpaste C is greater both at surface and deep within the teeth. Toothpaste K contains a lower concentration of sodium fluoride than Toothpaste C, yet Toothpaste K provided greater remineralization of teeth. Without wishing to be bound by theory, this result and finding may be due to the demineralization of enamel being inhibited by the concentration of fluoride in sub ppm range. Likewise, remineralization of incipient caries lesions may be accelerated by trace amounts of fluoride. Dental caries occurs when demineralization exceeds remineralization, resulting in hard tissue breakdown. A favorably shift to remineralization and repairs occurs by the introduction of the fluoride ion. The driving force for both phenomena is thermodynamic, that is, fuorapatite or a fluoridated hydroxyapatite may form when fluoride is supplied at low concentrations" (Critical Reviews in Oral Biology and Medicine, 1991, Vol. 2(2), pp. 283-296).

An unexpected discovery from this study is the combined effect of sodium myristoyl sarcosinate and stabilized chlorine dioxide (i.e., sodium chlorite or chlorite ion source) in a single-phase composition in achieving remineralization of teeth (combined result of enhanced remineralization and reduced demineralization) is greater than the combination of sodium lauroyl sarcosinate and sodium chlorite.

Example 12: Regrowth of Oral Polymicrobial Biofilm

The following study was performed to determine the relative effect of Exemplary Toothpaste K on preventing regrowth of oral biofilm comprising a mixed salivary bacterial preparation on bovine enamel surfaces. The data was compared between the toothpaste brushed samples and water brushed samples at regular intervals of time up to 24 hours. Data is reported for the relative number of adherent microorganisms after the regrowth time periods as detected by confocal microscopy.

Test Product: Exemplary Toothpaste K was prepared following the teaching as described herein.

Experimental Design: 4×4 mm bovine enamel sections (embedded in 12×12×7 mm acrylic resin) were prepared for use in sterile 12 well tissue culture plates and sterilized by ETO. 3 ml of Brain Heart Infusion broth supplemented with Yeast Extract and Vitamin K and hemin (BHI-YE) were inoculated with 50 µl of an overnight culture of a mixed species whole salivary bacterial prepared in the wells of the tissue culture plate containing the sections (1 section/well). The mixed species preparation was prepared by pooling equal volumes of whole saliva from three healthy human subjects and inoculating BHI-YE media, incubating for 24 hours and freezing in 15% glycerol at −80° C. until used. The species present included many typical oral bacteria species. These organisms were not speciated. The plates were incubated for 24 hours to grow the biofilm on the enamel. In order to remove the biofilm similar to a human subject brushing his/her teeth, three sections were brushed with the toothpaste or water using a brushing schedule similar to a 30 second brushing by human subjects. The sections were rinsed with sterile water and inserted into a fresh tissue culture plate containing 3 ml of BHI-YE to facilitate regrowth of the remaining oral biofilm on the enamel sections. The plates were re-incubated for 6, 12- and 24-hour time periods. The sections were removed at these time intervals and stained with a live/dead stain (BacLight Bacterial Viability Stain containing Syto9 and Propidium iodide) for confocal microscopy. Three samples brushed with either water or test toothpaste were run in triplicate (total sample size per group=9) at each time point. The Syto9 dye stains all live cells a green fluorescent color and Propidium iodide stains dead cells a red fluorescent color. The amount of green and red fluorescence was measured automatically using the confocal microscope software. The data are reported as the estimated mass of live and dead bacteria, the volume (area) of live and dead bacteria and the amount of low intensity stained red dead cells. Low intensity red cells may represent recently dead/compromised cells. Mass and volume of live cells relate to the intact biofilm and those of dead cells relate to compromised biofilm. This experimental method followed the standard methods for such a study found in the published literature (Huang, R., M. Li and R. L. Gregory. 2012. Effect of nicotine on growth and metabolism of *Streptococcus mutans*. Eur. J. Oral Sciences 120:319-325; Sabrah, A. H. A., G. H. Yassen, K. J. Spolnik, A. T. Hara, J. A. Platt and R. L. Gregory. 2015.) Evaluation of residual antibacterial effect of human radicular dentin treated with triple and double antibiotic pastes. J. Endodon. 41:1081-1084; and Huang, R., M. Li and R. L. Gregory. 2015. Nicotine promotes *Streptococcus mutans* extracellular polysaccharide synthesis, cell aggregation and overall lactate dehydrogenase activity. Archs. Oral Biol. 60:1083-1090).

Figure 5:
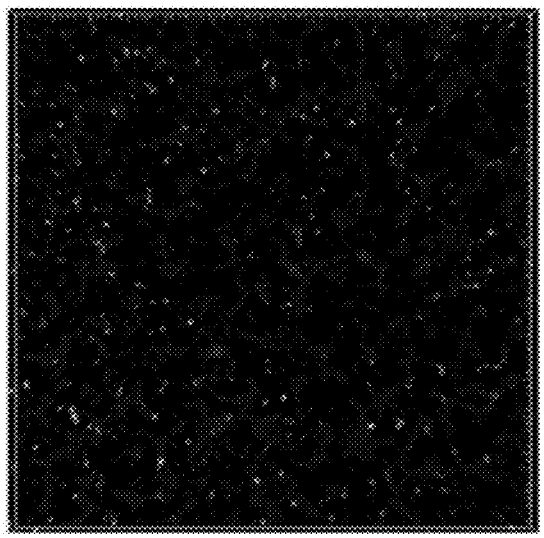
FIG. 5 illustrates confocal microscopy images of Toothpaste K and water brushed specimens after 6 h of brushing according to various embodiments.
Figure 5:
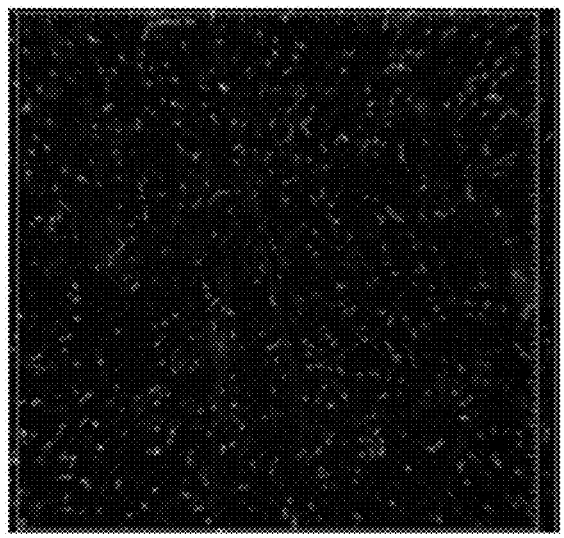

Results: Exemplary Toothpaste K was tested for its ability to prevent the regrowth of a mixed species biofilm 6, 12 and 24 hours after brushing compared to regrowth following brushing with water. The estimated mass (related to the number of cells) of the live bacterial cells (green stained) representing microbial biofilm and of dead bacterial cells (red stained) representing compromised biofilm were assessed using confocal microscopy. Three enamel specimens and three separate positions on each enamel surface were measured using live/dead staining by measuring the pixels on the confocal images. In addition, the volume (area of biofilm covered) of the green and red bacterial biofilm was determined for each specimen as well as the sum amount of low intensity stained red (dead) bacterial cells. Table 16 summarizes the individual values for each of these parameters as well as the mean and SD values. Furthermore, simple two group T tests were calculated comparing the paste treated specimens to water treated specimens. The results are presented in Table 16 and FIG. 5.

TABLE 16

Regrowth of Oral Polymicrobial Biofilm

| Hour | Sample (n = 9) | Estimated Live Cells Mean (SD) | p value | Estimated Dead Cells Mean (SD) | p value |
|---|---|---|---|---|---|
| 6 | Toothpaste K | 0.80E+08 (1.31E+08) | 0.0388 | 1.17E+08 (1.46E+08) | 0.1297 |
|   | Water | 3.66E+08 (3.35E+08) |  | 2.45E+08 (1.74E+08) |  |
| 12 | Toothpaste K | 2.83E+08 (2.65E+08) | 0.9787 | 2.80E+08 (2.32E+08) | 0.1989 |
|   | Water | 2.80E+08 (2.69E+08) |  | 5.51E+08 (5.22E+08) |  |
| 24 | Toothpaste K | 2.84E+07 (1.74E+07) | 0.0004 | 5.19E+08 (5.65E+08) | 0.0259 |
|   | Water | 0.14E+07 (0.158E+07) |  | 0.271E+08 (0.286E+08) |  |

The status of the biofilm as determined by number of live and dead cells at 6 hour, 12 hour and 24 hour time points after brushing and approximates the normal use of toothpaste by individuals. The estimated mass data for live cells (green stained) indicated that the paste significantly ($p=0.0388$) inhibited the mass of the live bacterial biofilm 6 hours after the biofilm was brushed when compared to the water brushed specimens. Images in FIG. 5 demonstrate that Exemplary Toothpaste K brushed specimen exhibited lesser number of live cells (green stained) compared to water brushed sample, demonstrating the reduced regrowth of polymicrobial biofilm as a result of effective removal of biofilm during brushing through the use of Toothpaste K. Therefore, the results demonstrate the Toothpaste K is highly effective killing bacteria in oral polymicrobial biofilm.

Example 13: Dental Abrasion

The following study was performed to determine the relative abrasion of dentin (or relative dentin abrasion, RDA) during brushing by tested toothpastes.

Test Products: Toothpaste C was prepared following the teachings of U.S. Patent Application Publication No. 2019/0070085. Exemplary Toothpaste K was prepared following the teaching as described herein. The American Dental Association (ADA) Reference Material was procured from Odontex Inc., Lawrence, Kans., USA.

Experimental Design: The procedure for determination of dentifrice Abrasivity is described in ISO 11609 and American National Standards Institute/American Dental Association (ANSI/ADA) Standard No. 130 as recommended by ADA. The human dentin specimens (n=8) were placed in a neutron flux under the controlled conditions outlined by the ADA. The specimens were then mounted in methyl methacrylate so they would fit in a V-8 cross-brushing machine. The specimens were brushed for a 1500-stroke precondition run using a slurry consisting of 10 g of ADA Reference Material in 50 ml of a 0.5% carboxymethyl cellulose (CMC) glycerin solution. The brushes used were those specified by the ASO/ADA (Oral-B, Procter and Gamble, Cincinnati, Ohio, USA) and brush tension was set to 150 g. Following a precondition run, the test was performed using 150 g and 1500 strokes in a sandwich design in which each toothpaste material slurry (25 g/40 ml for toothpastes) was flanked by the Reference Material slurries (10 g/50 ml 0.5% CMC) as outlined below in Table 17:

TABLE 17

| Run | Treatment |
|---|---|
| 1 | ADA Reference Material |
| 2 | Toothpaste C or Toothpaste K |
| 3 | ADA Reference Material |

One ml samples were taken and 0.01 g of this sample was added to 4.5 ml of scintillation cocktail. The samples were mixed well and immediately put on the scintillation counter for radiation detection. Following counting, the net CPM values were divided by the weight of the sample to calculate a net CPM/g of slurry. The net CPM/g of the pre- and post-ADA Reference Material for each test slurry were then calculated and averaged to use in the calculation of relative dentin abrasion (RDA) for tested toothpastes. The ADA Reference Material was assigned a value of 100 and its ratio to the test material was calculated.

Results: The RDA value for Toothpaste C and Exemplary Toothpaste K are presented in Table 18.

TABLE 18

Relative Dentin Abrasion (RDA) Values

| Toothpaste (n = 8) | RDA Value ± SEM |
|---|---|
| Toothpaste C | 207.55 ± 4.86 |
| Toothpaste K | 142.03 ± 2.50 |

American National Standards Institute/American Dental Association (ANSI/ADA) have set upper limit of 250 for RDA value (ANSI/ADA Standard No. 130:2013 Dentifrices—Requirements, Test Methods and Marking. 2013). Toothpastes having RDA value below 250 produce limited wear to dentin and are safe for use (Hunter M L, Addy M, Pickles M J, Joiner A. The Role of Toothpastes and Toothbrushes in the Aetiology of Tooth Wear. Int Dent J 2002; 52:399-405). Silica is an abrasive agent in both Toothpaste C and Toothpaste K. Also, the quality (grade) and concentration of silica are identical in both Toothpaste C and Exemplary Toothpaste K (Table 12). Given the comparable quality (grade) and concentration of silica in Toothpastes C and K, the RDA values would be anticipated to be equivalent. However, RDA value of Toothpaste K was significantly lower (by 65.55) than Toothpaste C. Lower Abrasivity of Toothpaste K is attributed to physico-chemical properties of sodium myristoyl sarcosinate and its interaction with other ingredients of the single-phase composition.

As discussed above, an unexpected discovery from this study is the combined effect of sodium myristoyl sarcosinate and stabilized source of chlorine dioxide in a single-phase composition in achieving lower RDA value (Abrasivity) than the combination of sodium lauroyl sarcosinate and stabilized source of chlorine dioxide.

Each of the exemplary compositions and those against which they were compared were suitable for use as a prophylactic treatment for cleaning the teeth, by applying the composition formulated as a paste to the tooth surface when disposed in a tube as employed by individuals in routine home oral hygiene procedures of tooth brushing.

The detailed descriptions above shows various embodiments of the composition, and by way of illustration, including the best mode of use of the embodiments. While these embodiments are described in sufficient detail to enable those skilled in the art to practice the principles of the present disclosure, it should be understood that other embodiments may be realized and that chemical changes may be made without departing from the spirit and scope of principles of the present disclosure. Thus, the detailed description herein is presented for purposes of illustration only and not of limitation. With regard to procedures, methods, techniques, and workflows that are in accordance with some embodiments, some operations in the procedures, methods, techniques, and workflows disclosed herein may be combined and/or the order of some operations may be changed. For example, the steps recited in any of the method descriptions may be executed in any suitable order and are not limited to the order presented.

In the above description, all cited references are incorporated herein by reference in their entireties. The citing of any reference is not an admission that such a reference is relevant prior art; rather, citations are to reference the novelty of the invention and discoveries described herein relative to known scientific literature, practices and prior art. In the description of the Present Invention, all ratios are weight ratios unless specifically stated otherwise. Unless otherwise indicated or evident from context, preferences indicated above and herein apply to the entirety of the embodiments discussed herein.

In describing the Present Invention, its embodiments and methods of use, the following terminology will be used: The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an items. The term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3 and 4 and sub-ranges such as 1-3, 2-4 and 3-5, etc.

This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

The scope should be determined by the appended claims and their legal equivalents, rather than by the examples given above. For example, the operations recited in any method claims may be executed in any order and are not limited to the order presented in the claims. Moreover, no element is essential unless specifically described herein as "critical" or "essential."

Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The invention claimed is:

1. A single-phase composition comprising:
   from about 0.01% to about 5.0% of N-acyl sarcosinate comprising sodium myristoyl sarcosinate, based on a total weight of the composition;
   from about 0.001 to about 8.0% of sodium chlorite, based on a total weight of the composition;
   a buffering system comprising disodium hydrogen phosphate and sodium dihydrogen phosphate; and water, wherein pH of the single phase composition is between 6.0 and 8.0, and wherein the single phase composition exhibits less than 35% loss of the sodium chlorite for a period of 24 months at about 25° C.

2. The single-phase composition of claim 1, wherein the sodium myristoyl sarcosinate provides enhanced stability for the sodium chlorite.

3. The single-phase composition of claim 1, wherein the single-phase composition is formulated into a form of, at least one of, a mouth rinse, a gum, a gel, a paste, a cream, spray, and a lozenge.

4. The single-phase composition of claim 1, further comprising an orally acceptable aqueous vehicle comprising, at least one of, a humectant, an abrasive, a pharmaceutically acceptable carrier, a fluoride ion source, dispersing agent and a thickening agent.

5. The single-phase composition of claim 1, wherein the single-phase composition oxidizes salivary biomolecules comprising pyruvate and L-methionine in 30 to 120 seconds of contact with saliva.

6. The single-phase composition of claim 1, wherein the single-phase composition is applied to, at least one of, anal, aural, nasal, oral, and urogenital cavities.

7. The single-phase composition of claim 1, wherein less than 20% of the sodium chlorite is degraded after 3 months at 40±1° C. and 70-75% relative humidity or one year under ambient conditions.

8. The single-phase composition of claim 1, wherein single-phase composition is formulated into a toothpaste, wherein the toothpaste has a relative dentin abrasion value in a range from 135 to 149.

9. A single-phase toothpaste comprising:
from about 0.01% to about 5.0% of N-acyl sarcosinate comprising sodium myristoyl sarcosinate, based on a total weight of
the single-phase toothpaste; from about 0.001 to about 8% of sodium chlorite, based on the total weight of the single-phase toothpaste; from about 0.01% to 0.21% of a fluoride ion source; a buffering system comprising disodium hydrogen phosphate and sodium dihydrogen phosphate; and water, wherein pH of the single-phase toothpaste is between 6.0 and 8.0, and wherein the single phase toothpaste exhibits less than 35% loss of the sodium chlorite for a period of 24 months at about 25° C.

10. The single-phase toothpaste of claim 9, wherein the sodium myristoyl sarcosinate provides enhanced stability for the sodium chlorite in the single-phase toothpaste.

11. The single-phase toothpaste of claim 9, further comprising at least one material selected from a group consisting of a humectant, a whitening agent, a thickening agent, a fluoride ion source, a sweetening agent, an abrasive, a flavoring agent, a coloring agent, and a gelling agent.

12. The single-phase toothpaste of claim 9, wherein less than 20% of the sodium chlorite is degraded in 3 months at 40±1° C. and 70-75% relative humidity or one year under ambient conditions.

13. The single-phase toothpaste of claim 9, wherein the fluoride ion source comprises at least one of indium fluoride, sodium fluoride, silver diamine fluoride, stannous fluoride or sodium monofluorophosphate.

14. The single-phase toothpaste of claim 9, wherein the toothpaste decreases regrowth of an oral polymicrobial biofilm in 6 hours after brushing.

15. The single-phase toothpaste of claim 9, wherein the toothpaste enhances remineralization of a tooth enamel.

16. The single-phase toothpaste composition of claim 9, wherein the toothpaste enhances fluoride uptake on a tooth enamel.

17. The single-phase toothpaste of claim 9, wherein the toothpaste oxidizes salivary biomolecules comprising pyruvate and L-methionine in 30 to 60 seconds of contact with the saliva in the oral cavity.

18. A method for enhancing remineralization of tooth enamel into an oral cavity, comprising:
obtaining the single-phase composition of claim 1, and applying the single-phase composition to the oral cavity regularly for 10 to 20 days.

19. A method for preparing the of single-phase composition of claim 1, comprising steps of stirring a gelling agent into water; followed by stirring in buffering compounds comprising disodium hydrogen phosphate and sodium dihydrogen phosphate until a pH of 6.0 to 8.0 is achieved; stirring in a sodium chlorite aqueous solution;
stirring in one by one at least one of a humectants, sweetening agent, coloring agent, abrasive agent, fluoride ion source, flavoring agent, emollient agent, and emulsifying agent; adding N-acyl sarcosinate comprising sodium myristoyl sarcosinate,
and stirring the composition under vacuum for about 45 minutes; wherein all the steps are carried out at room temperature,
and dispensing the composition into tubes after the vacuum is released.

20. The single-phase toothpaste of claim 1, wherein the single-phase toothpaste exhibits enhanced bioavailability within 30 seconds to 120 seconds and wherein the single-phase toothpaste exhibits enhanced plaque reduction and plaque removal.

* * * * *